United States Patent

Yano et al.

[11] Patent Number: 6,146,718
[45] Date of Patent: Nov. 14, 2000

[54] LIQUID CRYSTALLINE COMPOUND HAVING A NEGATIVE DIELECTRIC ANISOTROPY VALUE, LIQUID CRYSTAL COMPOSITION CONTAINING THE LIQUID CRYSTALLINE COMPOUND, AND LIQUID CRYSTAL DISPLAY ELEMENT PRODUCED UTILIZING THE LIQUID CRYSTAL COMPOSITION

[75] Inventors: Hitoshi Yano; Shuichi Matsui; Hiroyuki Takeuchi; Kazutoshi Miyazawa, all of Ichihara; Yasuhiro Haseba, Matsudo, all of Japan

[73] Assignee: Chisso Corporation, Osaka, Japan

[21] Appl. No.: 09/135,816

[22] Filed: Aug. 18, 1998

[30] Foreign Application Priority Data

Jun. 10, 1998 [JP] Japan .................................. 10-178135

[51] Int. Cl.$^7$ .......................... C09K 19/30; C09K 19/34; G02F 1/13; C07D 309/02; C07D 315/00
[52] U.S. Cl. .................. 428/1; 252/299.61; 252/299.62; 252/299.63; 549/428
[58] Field of Search .......................... 252/299.61, 299.62, 252/299.63; 549/428, 416, 425, 427; 428/1

[56] References Cited

FOREIGN PATENT DOCUMENTS 9832721  7/1998  WIPO .

OTHER PUBLICATIONS

CA 129: 129082, 1998.

CA 105: 190850, 1985.

Ca 79: 66277, 1973.

CA 73: 119856, 1970.

*Primary Examiner*—Shean C. Wu
*Attorney, Agent, or Firm*—Browdy and Neimark

[57] ABSTRACT

The present invention provides a liquid crystal compound having a negative dielectric constant anisotropy value of a large absolute value, a controlled optically anisotropy value, a high resistivity, a high voltage retention, and high stability against heat and ultraviolet radiation; a liquid crystal composition containing such a liquid crystal compound; and a liquid crystal display element fabricated from such a liquid crystal composition.

There is disclosed a liquid crystal compound having 6,6-difluorotetrahydropyran-2,5-diyl, 6,6-difluoro-2,3-dihydro-6H-pyran-2,5-diyl, and/or 6-fluoro-3,4-dihydro-2H-pyran-2,5-diyl in the skeleton thereof; a liquid crystal composition containing such a liquid crystal compound; and a liquid crystal display element fabricated from such a liquid crystal composition.

20 Claims, No Drawings

LIQUID CRYSTALLINE COMPOUND HAVING A NEGATIVE DIELECTRIC ANISOTROPY VALUE, LIQUID CRYSTAL COMPOSITION CONTAINING THE LIQUID CRYSTALLINE COMPOUND, AND LIQUID CRYSTAL DISPLAY ELEMENT PRODUCED UTILIZING THE LIQUID CRYSTAL COMPOSITION

TECHNICAL FIELD

The present invention relates to a novel liquid crystalline compound exhibiting properties suitable for liquid crystal compositions chiefly used in liquid crystal display elements of, for example, the vertical orientation system or various display systems, such as in-plain switching (IPS), the thin film transistor (TFT), twisted nematic (TN), or super twisted nematic (STN) systems, particularly in the vertical orientation system and the ISP display system; a liquid crystal composition containing such a liquid crystalline compound and having favorable properties; and a liquid display element produced utilizing such a liquid crystal composition. The term "liquid crystalline compound" used herein is a generic term for compounds which exhibit a liquid crystal phase, as well as compounds which do not exhibit a liquid crystal phase but which are useful as the components of liquid crystal compositions.

BACKGROUND ART

Heretofore, various liquid crystal display systems have been proposed. Examples of these systems include the following (refer to "The Latest Technology of Liquid Crystals," edited by Kogyo Chosa-kai (1983)). Systems which use liquid crystal compositions having positive dielectric anisotropy values include TN and STN systems, or active matrix (AM) (TFT or metal-insulation film-metal (MIM)) systems based on the TN mode. Systems which use liquid crystal compositions having negative dielectric anisotropy values include the ECB (HAN or DAP), DS, GH, and PC systems.

Of these systems, the system using liquid crystal compositions having positive dielectric anisotropy values constitutes the mainstream of practical use. In comparison, practical use of the system using liquid crystal compositions having negative dielectric anisotropy values has been delayed. In the light of the above, the development of liquid crystal compositions having negative dielectric anisotropy values and compounds used for producing such compositions is insufficient relative to the development of liquid crystal compositions having positive dielectric anisotropy values.

Under this situation, recent efforts have been made to improve the viewing angle, which is one of the shortcomings of liquid crystal displays. One system which addresses this fault is IPS (R. Kiefer et al., JAPAN DISPLAY '92, 547 (1992), M. Oh-e et al., ASIA DISPLAY '95, 577 (1995), Japanese Patent Application Laid-open No.5-505247, Japanese Patent Application Laid-open No. 7-128647, etc.). One of the features of IPS used in the liquid crystal panel of the cited invention is that a comb-shaped electrode is provided on only one side of substrates, whereas in conventional liquid crystal panels an electrode is provided on each of upper and lower substrates. Another feature of the cited invention is that the liquid crystal composition can be used regardless of whether the dielectric anisotropy value is positive or negative.

Another fruit of the efforts to improve the viewing angle is a system utilizingthe vertical orientation of liquid crystal molecules (Japanese Patent Application Laid-open No. 2-176625). One of the features of this system is the use of liquid crystal compositions having negative dielectric anisotropy values.

In view of such a background, liquid crystalline compounds and liquid crystal compositions having negative dielectric anisotropy values have been strongly desired.

In liquid crystal compositions used in display systems, not only dielectric anisotropy values, but also other properties, such as optical anisotropy values ($\Delta n$) and elastic coefficient ratio $K_{33}/K_{11}$ ($K_{33}$: bend elastic coefficient, $K_{11}$: spray elastic coefficient), should be adjusted to optimal values, and furthermore, the liquid crystal phase must exist in an adequate temperature range, and the composition must have a low viscosity even at low temperature.

Among conventionally known liquid crystalline compounds, none satisfy all of these requirements. Therefore, compositions which can be used as a liquid crystal are obtained by mixing several to more than 20 kinds of species of compounds having liquid crystal phases, and, when desired, several types of compounds having no liquid crystal phases. Therefore, each liquid crystalline compound to be mixed is required properties such as high miscibility with other liquid crystalline compounds and high miscibility at a low temperature region for use at low temperature.

However, since as described above the mainstream of conventional display systems has involved the use of liquid crystal compositions containing liquid crystalline compounds having positive dielectric anisotropy values, the development of liquid crystal compounds or compositions having negative dielectric anisotropy values has not been sufficient. Therefore, conventional liquid crystalline compounds and compositions have been unable to support such diversified systems and satisfy accompanying requirements for various properties. For example, in a conventional liquid crystal composition, even if $\Delta \epsilon$ is negative, its absolute value is small;

since the elastic coefficient is high, the driving voltage cannot be lowered;

since miscibility is poor, such a compound cannot be used in a large quantity;

the optical anisotropy values cannot be set freely;

the viscosity is high; and chemical and physical stability is poor.

Prior to the present invention, compounds having 2,2-difluorocyclohexane-1,4-diyl, 6-fluorocyclohexene-1,4-diyl, or 2-fluorocyclohexene-1,4-diyl skeletons have been reported (Japanese Patent Application Laid-open Nos. 5-279279 and 8-12604, and German Patent Publication No. 4427266A1). However, these patents do not describe any of the properties that such compounds required for use for preparing liquid crystal compositions; for example, adequate $\Delta \epsilon$ and $\Delta n$, low elastic coefficients, high miscibility, low viscosity, and high chemical and physical stability.

Also, these patents do not express the idea of converting cyclohexane skeletons to pyran skeletons in order to derive liquid crystal compounds having negative $\Delta \epsilon$ from the compounds having 2,2-difluorocyclohexane-1,4-diyl, 6-fluorocyclohexene-1,4-diyl, or 2-fluorocyclohexene-1,4-diyl skeletons. Thus, the compound of the present invention cannot be derived easily from prior art.

The object of the present invention is to solve the problems described above, and to provide a novel liquid crystalline compound, a liquid crystal composition containing the liquid crystalline compound,, and a liquid crystal display element fabricated utilizing the liquid crystal composition, which can be used in a vertical orientation system as described in Japanese Patent Application Laid-open No.2-176625 and in various display systems using compounds or compositions having negative $\Delta\epsilon$ values, such as IPS, ECB (HAN or DAP), DS, GH, or PC, as well as for the adjustment of properties of liquid crystal compositions for various display systems using compounds or compositions having positive $\Delta\epsilon$ values, such as TN, STN, or AM (TFT or MIM) based on the TN mode.

DISCLOSURE OF THE INVENTION

The present inventors conducted repeated examinations for solving the above problems, and found that compounds having partial structures consisting of 6,6-difluorotetrahydropyran-2,5-diyl, 6,6-difluoro-2,3-dihydro-6H-pyran-2,5-diyl, and/or 6-fluoro-3,4-dihydro-2H-pyran-2,5-diyl have not only negative $\Delta\epsilon$ values, but also adequate $\Delta n$ values, high miscibility, low viscosity, and high chemical and physical stability; that by the use of compounds having partial structures consisting of 6,6-difluorotetrahydropyran-2,5-diyl, 6,6-difluoro-2,3-dihydro-6H-pyran-2,5-diyl, and/or 6-fluoro-3,4-dihydro-2H-pyran-2,5-diyl there can be obtained liquid crystal compositions having low elastic constant, $\Delta\epsilon$ and $\Delta n$ that can be adjusted adequately, low viscosity, and high chemical and physical stability; in particular, liquid crystal compositions having negative $\Delta\epsilon$ values of a large absolute value; and that a liquid crystal display element can be fabricated utilizing such compositions.

According to a first aspect of the present invention, there is provided a liquid crystalline compound having a structure comprising 6,6-difluorotetrahydropyran-2,5-diyl, 6,6-difluoro-2,3-dihydro-6H-pyran-2,5-diyl, and/or 6-fluoro-3,4-dihydro-2H-pyran-2,5-diyl in the skeleton thereof.

According to a second aspect of the present invention, there is provided a liquid crystalline compound according to the first aspect represented by general formula (1), (1)

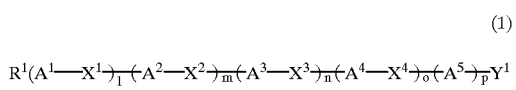

where, $R^1$ and $Y^1$ independently represent an alkyl group having 1 to 20 carbon atoms, a hydrogen atom, a halogen atom, a cyano group, a cyanate group, an isocyano group, or an isothiocyanate group, in which one or more nonadjacent methylene groups in said alkyl group may be substituted by an oxygen atom, a sulfur atom, a nitrogen atom, —C≡C—, a dialkylsilylene group, a monoalkylsilylene group, a silylene group, or a vinylene group, and one or more hydrogen atoms in the alkyl group may be substituted by a fluorine atom or a chlorine atom; $X^1$, $X^2$, $X^3$, and $X^4$ independently represent a single bond, —(CH$_2$)$_2$—, —CH=CH—, —C≡C—, —COO—, —OCO—, —CH$_2$O—, —OCH$_2$—, —(CH$_2$)$_4$—, —(CH$_2$)$_3$O—, —O(CH$_2$)$_3$—, —CH=CHCH$_2$CH$_2$—, —CH$_2$CH=CHCH$_2$—, —CH$_2$CH$_2$CH=CH—, —CH=CHCH=CH—, —CF$_2$O—, —OCF$_2$—, —CH=CHCH$_2$O—, —OCH$_2$CH=CH—, —CF=CF—, —CH$_2$CF$_2$—, —CF$_2$CH$_2$—, —(CF$_2$)$_2$—, —(CF$_2$)$_4$—, —(CH$_2$)$_2$COO—, —OCO(CH$_2$)$_2$—, —CH=CHCOO—, —OCOCH=CH—, —CH=CHC≡C— or —C≡CCH=CH—; ring $A^1$, ring $A^2$, ring $A^3$, ring $A^4$, and ring $A^5$ independently represent trans-cyclohexane-1,4-diyl, cyclohexa-1-ene-1,4-diyl, 1,4-phenylene, bicyclo[1.1.1] pentane-1,3-diyl, 6,6-difluorotetrahydropyran-2,5-diyl, 6,6-difluoro-2,3-dihydro-6H-pyran-2,5-diyl, or 6-fluroro-3,4-dihydro-2H-pyran-2,5-diyl, in which carbon atoms constituting these rings may be substituted by nitrogen atoms, oxygen atoms, or sulfur atoms, and hydrogen atoms on the ring may be substituted by halogen atoms or cyano groups, but at least one of said rings $A^1$, $A^2$, $A^3$, $A^4$, and $A^5$ is 6,6-difluorotetrahydropyran-2,5-diyl, 6,6-difluoro-2,3-dihydro-6H-pyran-2,5-diyl, or 6-fluroro-3,4-dihydro-2H-pyran-2,5-diyl; l, m, n, o, and p are independently 0 or 1, but l+m+n+o+p≧1; and any atom of this compound may be substituted by an isotope thereof.

According to a third aspect of the present invention, there is provided a liquid crystal composition containing at least one of the liquid crystalline compounds according to the first or second aspect.

According to a fourth aspect of the present invention, there is provided a liquid crystal composition containing as the first component thereof at least one of the liquid crystalline compounds according to the first or second aspect, and as the second component thereof at least one of the compounds selected from the group consisting of compounds represented by general formulas (2), (3), and (4), (2)

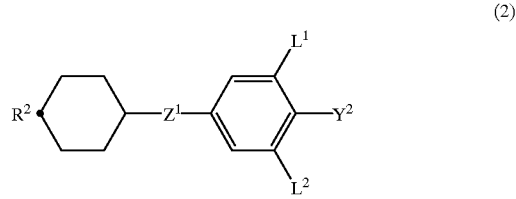

(3)

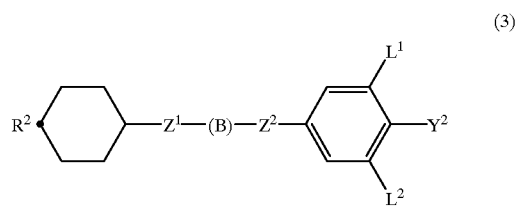

(4)

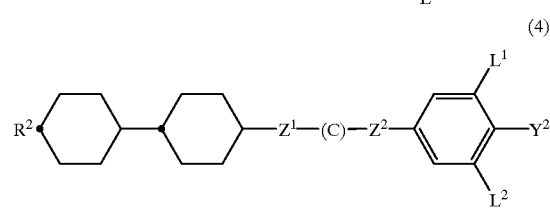

where, $R^2$ represents an alkyl group having 1 to 10 carbon atoms, in which one or more nonadjacent methylene groups in said alkyl group may be substituted by an oxygen atom or —C=C—, and one or more hydrogen atom in the alkyl group may be substituted by a fluorine atom; $Y^2$ represents a fluorine atom, a chlorine atom, —OCF$_3$, —OCF$_2$H, —CF$_3$, —CF$_2$H, —CFH$_2$, —OCF$_2$CF$_2$H, or —OCF$_2$CFHCF$_3$; $L^1$ and $L^2$ independently represent a hydrogen atom or a fluorine atom; $Z^1$ and $Z^2$ independently represent —(CH$_2$)$_2$—, —(CH$_2$)$_4$—, —COO—, —CF$_2$O—, —OCF$_2$—, —CH=CH—, or a single bond; ring B represents trans-cyclohexane-1,4-diyl, 1,3-dioxane-2,5-diyl, or 1,4-phenylene whose hydrogen atoms may be substituted by fluorine atoms; ring C represents trans-cyclohexane-1,4-diyl, or 1,4-phenylene whose hydrogen atoms may be substituted by fluorine atoms; and any atom of this compound may be substituted by an isotope thereof.

According to a fifth aspect of the present invention, there is provided a liquid crystal composition containing as the first component thereof at least one of the compounds according to the first or second aspect, and as the second component thereof at least one of the compounds selected from the group consisting of compounds represented by general formulas (5) and (6),

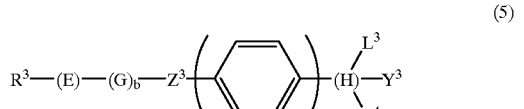

(5)

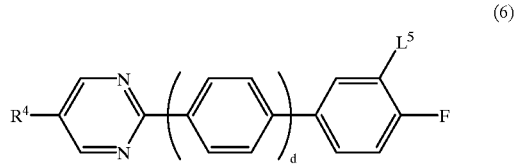

(6)

where, $R^3$ and $R^4$ independently represent an alkyl group having 1 to 10 carbon atoms, in which one or more nonadjacent methylene groups in said alkyl group may be substituted by an oxygen atom or —C≡C—, and one or more hydrogen atoms in the alkyl group may be substituted by a fluorine atom; $Y^3$ is a cyano group or —C≡C—CN; ring E represents trans-cyclohexane-1,4-diyl, 1,4-phenylene, 1,3-dioxane-2,5-diyl, or pyrimidine-2,5-diyl; ring G represents trans-cyclohexane-1,4-diyl, pyrimidine-2,5-diyl or 1,4-phenylene whose hydrogen atoms may be substituted by fluorine atoms; ring H represents trans-cyclohexane-1,4-diyl or 1,4-phenylene; $Z^3$ represents —(CH$_2$)$_2$—, —COO—, or a single bond; $L^3$, $L^4$, and $L^5$ independently represent a hydrogen atom or a fluorine atom; b, c, and d independently represent 0 or 1; and any atom of this compound may be substituted by an isotope thereof.

According to a sixth aspect of the present invention, there is provided a liquid crystal composition containing as the first component thereof at least one of the compounds according to the first or second aspect, as the second component thereof at least one of the compounds selected from the group consisting of compounds represented by general formulas (2), (3), and (4), and as the third component thereof at least one of the compounds selected from the group consisting of compounds represented by general formulas (7), (8), and (9),

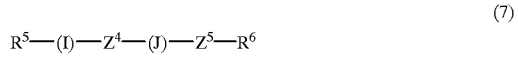

(7)

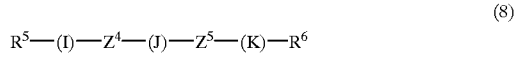

(8)

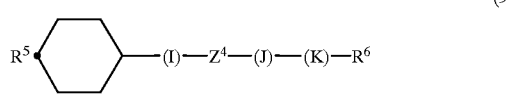

(9)

where, $R^5$ and $R^6$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group may be substituted by a fluorine atom; rings I, J, and K independently represent trans-cyclohexane-1,4-diyl, pyrimidine-2,5-diyl or 1,4-phenylene whose hydrogen atoms may be substituted by fluorine atoms; $Z^4$ and $Z^5$ independently represent —C≡C—, —COO—, —(CH$_2$)$_2$—, —CH═CH—, or a single bond; and any atom of this compound may be substituted by an isotope thereof.

According to a seventh aspect of the present invention, there is provided a liquid crystal composition containing as the first component thereof at least one of the compounds according to the first or second aspect, and as the second component thereof at least one of the compounds selected from the group consisting of compounds represented by general formulas (10), (11), and (12),

(10)

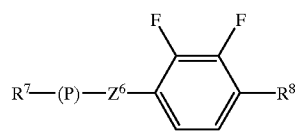

(11)

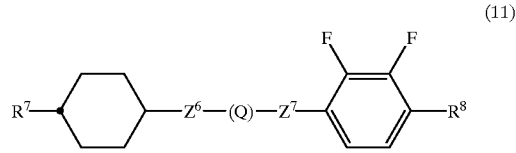

(12)

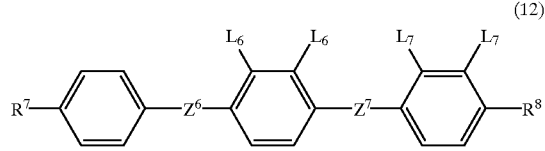

where, $R^7$ and $R^8$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group may be substituted by a fluorine atom; rings P and Q independently represent trans-cyclohexane-1,4-diyl or 1,4-phenylene; L6 and L7 independently represent a hydrogen atom or a fluorine atom, but do not represent hydrogen atoms at the same time; $Z^6$ and $Z^7$ independently represent —(CH$_2$)$_2$—, —COO—, or a single bond; and any atom of this compound may be substituted by an isotope thereof.

According to an eighth aspect of the present invention, there is provided a liquid crystal composition containing as the first component thereof at least one of the compounds according to the first or second aspect, as the second component thereof at least one of the compounds selected from the group consisting of compounds represented by general formulas (7), (8), and (9), and as the third component thereof at least one of the compounds selected from the group consisting of compounds represented by general formulas (10), (11), and (12).

According to a ninth aspect of the present invention, there is provided a liquid crystal composition containing as the first component thereof at least one of the compounds according to the first or second aspect, as the second component thereof at least one of the compounds selected from the group consisting of compounds represented by general formulas (5) and (6), and as the third component thereof at least one of the compounds selected from the group consisting of compounds represented by general formulas (7), (8), and (9).

According to a tenth aspect of the present invention, there is provided a liquid crystal composition containing as the first component thereof at least one of the compounds according to the first or second aspect, as the second component thereof at least one of the compounds selected from the group consisting of compounds represented by general formulas (2), (3), and (4), as the third component thereof at least one of the compounds selected from the group consisting of compounds represented by general formulas (5) and (6), and as the fourth component thereof at least one of the compounds selected from the group consisting of compounds represented by general formulas (7), (8), and (9).

According to an eleventh aspect of the present invention, there is provided a liquid crystal composition containing at least one optically active compound in addition to a liquid crystal composition according to any of the third through tenth aspects.

According to a twelfth aspect of the present invention, there is provided a liquid crystal display element fabricated utilizing a liquid crystal composition according to any of the third through eleventh aspects.

The seventh and eighth aspects of the present invention relate to N-type (negative $\Delta\epsilon$) liquid crystal compositions. The N-type liquid crystal compositions are driven by the vertical orientation system as described in Japanese Patent Application Laid-open No. 2-176625, or by any of various display systems such as IPS.

Although the fourth, fifth, sixth, ninth, and tenth aspects of the present invention relate to P-type (positive $\Delta\epsilon$) liquid crystal compositions, N-type compounds may be used as the components of such P-type liquid crystal compositions. By virtue of incorporation of N-type compounds into P-type compositions, not only can the $\Delta\epsilon$ be set freely to meet the purpose of the liquid crystal composition, but also other properties such as the $\Delta n$ or elastic coefficients can be controlled.

A preferred embodiment of the present invention will be described below. $R^1$ and $Y^1$ independently represent an alkyl group having 1 to 20 carbon atoms, a hydrogen atom, a halogen atom, a cyano group, a cyanate group, an isocyano group, or an isothiocyanate group, in which one or more nonadjacent methylene groups in said alkyl group may be substituted by an oxygen atom, a sulfur atom, a nitrogen atom, —C≡C—, a dialkylsilylene group, a monoalkylsilylene group, a silylene group, or a vinylene group, one or more hydrogen atoms in the alkyl group may be substituted by a fluorine atom or a chlorine atom, and the alkyl groups may be optically active.

In general formula (1), alkyl groups represented by $R^1$ and $Y^1$ specifically include saturated alkyl groups composed of only carbon and hydrogen atoms, as well as haloalkyl, alkoxy, haloalkoxy, alkenyl, haloalkenyl, alkenyloxy, haloalkenyloxy, alkinyl, haloalkinyl, alkinyloxy, haloalkinyloxy, alkoxyalkyl, haloalkoxyalkyl, alkoxyalkoxy, haloalkoxyalkoxy, alkanoyl, haloalkanoyl, alkanoyloxy, haloalkanoyloxy, alkoxycarbonyl, and haloalkoxycarbonyl groups.

Specific examples of $R^1$ and $Y^1$ include the following groups and atoms:

—$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$CFH_2$, —$CF_2H$, —$CF_3$, —$CH_2CH_2F$, —$CH_2CHF_2$, —$CH_2CF_3$, —$CF_2CH_3$, —$CF_2CF_2H$, —$CFHCF_3$, —$CF_2CF_3$, —$(CH_2)_2CH_2F$, —$(CH_2)_2CHF_2$, —$(CH_2)_2CF_3$, —$CH_2CF_2CH_3$, —$CH_2CF_2CF_3$, —$CF_2C_2H_5$, —$C_3F_7$, —$CF_2CFHCF_3$, —$(CH_2)_3CH_2F$, —$(CH_2)_4CH_2F$, —$(CH_2)_5CH_2F$, —$CF_2C_3H_7$, —$CH_2CF_2C_2H_5$, —$(CH_2)_2CF_2CH_3$, —$CF_2C_4H_9$, —$CH_2CF_2CH_3$, —$(CH_2)_2CF_2C_2H_5$, —$(CH_2)_3CF_2CH_3$,

—$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$, —$OCFH_2$, —$OCF_2H$, —$OCF_3$, —$OCH_2CH_2F$, —$OCH_2CHF_2$, —$OCH_2CF_3$, —$OCF_2CH_3$, —$OCF_2CF_2H$, —$OCFHCF_3$, —$OCF_2CF_3$, —$O(CH_2)_2CH_2F$, —$O(CH_2)_2CHF_2$, —$O(CH_2)_2CF_3$, —$OCH_2CF_2CH_3$, —$OCH_2CF_2CF_3$, —$OCF_2C_2H_5$, —$OC_3F_7$, —$OCF_2CFHCF_3$, —$O(CH_2)_3CH_2F$, —$O(CH_2)_4CH_2F$, —$O(CH_2)_5CH_2F$, —$OCF_2C_3H_7$, —$OCH_2CF_2C_2H_5$, —$O(CH_2)_2CF_2CH_3$, —$OCF_2C_4H_9$, —$OCH_2CF_2CH_3$, —$O(CH_2)_2CF_2C_2H_5$, —$O(CH_2)_3CF_2CH_3$,

—$CH=CH_2$, —$CH=CHCH_3$, —$CH=CHC_2H_5$, —$CH=CHC_3H_7$, —$CH=CHC_4H_9$, —$CH_2CH=CHCH_3$, —$CH_2CH=CHC_2H_5$, —$CH_2CH=CHC_3H_7$, —$CH_2CH=CHC_4H_9$, —$(CH_2)_2CH=CHCH_3$, —$(CH_2)_2CH=CHC_2H_5$, —$(CH_2)_2CH=CHC_3H_7$, —$(CH_2)_2CH=CHC_4H_9$, —$CH_2CH=CH_2$, —$(CH_2)_2CH=CH_2$, —$(CH_2)_3CH=CH_2$, —$(CH_2)_4CH=CH_2$, —$(CH_2)_5CH=CH_2$, —$CH=CHCH=CH_2$, —$CH=CHCH_2CH=CH_2$, —$CH=CH(CH_2)_2CH=CH_2$, —$CH=CH(CH_2)_3CH=CH_2$, —$CH_2CH=CH(CH_2)_2CH=CH_2$, —$(CH_2)_2CH=CH(CH_2)_2CH=CH_2$,

—$CF=CF_2$, —$CH=CF_2$, —$CH=CHF$, —$CH_2CF=CF_2$, —$CH_2CH=CFH$, —$(CH_2)_2CH=CF_2$, —$(CH_2)_2CH=CHF$, —$(CH_2)_3CH=CF_2$, —$(CH_2)_3CH=CHF$, —$(CH_2)_4CH=CF_2$, —$(CH_2)_4CH=CHF$, —$(CH_2)_5CH=CF_2$, —$(CH_2)_5CH=CHF$, —$CH=CHCH_2CH_2F$, —$CH=CHCH_2CH_2Cl$, —$CH=CHCH_2CHF_2$, —$CH=CHCH_2CF_3$, —$CH=CH(CH_2)_2CH_2F$, —$CH=CH(CH_2)_2CHF_2$,

—$CH=CH(CH_2)_2CF_3$, —$CH=CH(CH_2)_3CH_2F$, —$CH=CH(CH_2)_3CHF_2$, —$CH=CH(CH_2)_3CF_3$, —$CH=CH(CH_2)_4CH_2F$, —$CH=CH(CH_2)_4CHF_2$, —$CH=CH(CH_2)_4CF_3$, —$CH_2CH=CH(CH_2)_2CH_2F$, —$CH_2CH=CHCH_2CH_2F$, —$(CH_2)_2CH=CH(CH_2)_2CH_2F$, —$(CH_2)_2CH=CHCH_2CH_2F$, —$CH=CHCH_2CH=CF_2$, —$CH=CH(CH_2)_2CH=CF_2$, —$CH=CH(CH_2)_2CF=CF_2$, —$CH=CH(CH_2)_3CHFCH_3$,

—$OCH_2CH=CHCH_3$, —$OCH_2CH=CHC_2H_5$, —$OCH_2CH=CHC_3H_7$, —$OCH_2CH=CHC_4H_9$, —$O(CH_2)_2CH=CHCH_3$, —$O(CH_2)_2CH=CHC_2H_5$, —$O(CH_2)_2CH=CHC_3H_7$, —$O(CH_2)_2CH=CHC_4H_9$, —$OCH_2CH=CH_2$, —$O(CH_2)_2CH=CH_2$, —$O(CH_2)_3CH=CH_2$, —$O(CH_2)_4CH=CH_2$, —$O(CH_2)_5CH=CH_2$, —$OCH_2CH=CH(CH_2)_2CH=CH_2$, —$O(CH_2)_2CH=CH(CH_2)_2CH=CH_2$,

—$OCH_2CF=CF_2$, —$OCH_2CH=CF_2$, —$OCH_2CF=CHF$, —$O(CH_2)_2CH=CF_2$, —$O(CH_2)_2CH=CHF$, —$O(CH_2)_3CH=CF_2$, —$O(CH_2)_3CH=CHF$, —$O(CH_2)_4CH=CF_2$, —$O(CH_2)_4CH=CHF$, —$O(CH_2)_5CH=CF_2$, —$O(CH)_5CH=CHF$, —$OCH_2CH=CHCH_2CH_2F$, —$O(CH_2)_2CH=CH(CH_2)_2CH_2F$, —$O(CH_2)_2CH=CHCH_2CH_2F$,

—$C\equiv CH$, —$C\equiv CCH_3$, —$C\equiv CC_2H_5$, —$C\equiv CC_3H_7$, —$C\equiv CC_4H_9$, —$CH_2C\equiv CH$, —$CH_2C\equiv CCH_3$, —$CH_2C\equiv CC_2H_5$, —$CH_2C\equiv CC_3H_7$, —$CH_2C\equiv CC_4H_9$, —$(CH_2)_2C\equiv CH$, —$(CH_2)_2C\equiv CCH_3$, —$(CH_2)_2C\equiv CC_2H_5$, —$(CH_2)_2C\equiv CC_3H_7$, —$(CH_2)_2C\equiv CC_4H_9$, —$(CH_2)_3C\equiv CH$, —$(CH_2)_3C\equiv CCH_3$, —$(CH_2)_3C\equiv CC_2H_5$, —$(CH_2)_3C\equiv CC_3H_7$, —$(CH_2)_3C\equiv CC_4H_9$, —$C\equiv CCF_3$, —$C\equiv CC_2F_5$, —$C\equiv CC_3F_7$, —$CH_2C\equiv CCF_3$, —$(CH_2)_2C\equiv CCF_3$, —$OCH_2C\equiv CH$, —$OCH_2C\equiv CCH_3$, —$OCH_2C\equiv CC_2H_5$, —$OCH_2C\equiv CC_3H_7$, —$OCH_2C\equiv CC_4H_9$, —$O(CH_2)_2C\equiv CH$, —$O(CH_2)_2C\equiv CCH_3$, —$O(CH_2)_2C\equiv CC_2H_5$, —$O(CH_2)_2C\equiv CC_3H_7$, —$O(CH_2)_2C\equiv CC_4H_9$,

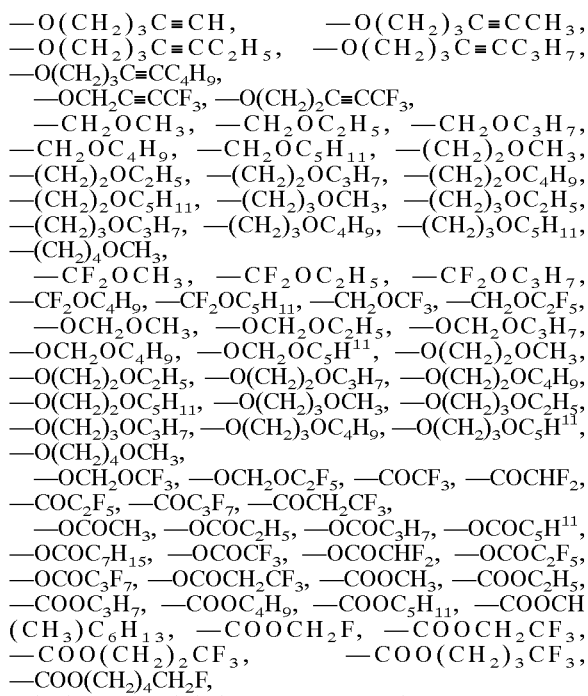

hydrogen and halogen atoms, and cyano, cyanate, isocyanate, and isothiocyanate groups.

When the chemical and physical stability of the compounds represented by general formula (1) is especially required, $R^1$ and $Y^1$ are preferably selected from the group consisting of saturated alkyl groups composed of only carbon and hydrogen atoms, haloalkyl, alkoxy, haloalkoxy, alkoxyalkyl, haloalkoxyalkyl, alkoxyalkoxy, haloalkoxyalkoxy, alkanoyl, haloalkanoyl, alkanoyloxy, haloalkanoyloxy, alkoxycarbonyl, and haloalkoxycarbonyl groups, hydrogen and halogen atoms, and cyano, cyanate, and isocyanate groups.

When a larger absolute value of the negative Δε of the compounds represented by general formula (1) is desired, $R^1$ and $Y^1$ are preferably those of substituting groups having a low polarity selected from the group consisting of saturated alkyl groups composed of only carbon and hydrogen atoms, alkoxy, alkenyl, alkenyloxy, alkinyl, alkinyloxy, alkoxyalkyl, alkoxyalkoxy, alkanoyl, alkanoyloxy, alkoxycarbonyl, and a hydrogen atom.

$X^1$, $X^2$, $x^3$, and $X^4$ of the compounds represented by general formula (1) are single bonds, —(CH$_2$)$_2$—, —CH=CH—, —C≡C—, —COO—, —OCO—, —CH$_2$O—, —OCH$_2$—, —(CH$_2$)$_4$—, —(CH$_2$)$_3$O—, —O(CH$_2$)$_3$—, —CH=CHCH$_2$CH$_2$—, —CH$_2$CH=CHCH$_2$—, —CH$_2$CH$_2$CH=CH—, —CH=CH—CH=CH—, —CF$_2$O—, —OCF$_2$—, —CH=CHCH$_2$O—, —OCH$_2$CH=CH—, —CF=CF—, —CH$_2$CF$_2$—, —CF$_2$CH$_2$—, —(CF$_2$)$_2$—, —(CF$_2$)$_4$—, —(CH$_2$)$_2$COO—, —OCO(CH$_2$)$_2$—, —CH=CHCOO—, —OCOCH=CH—, —CH=CHC≡C—, or —C≡CCH=CH—.

When the chemical and physical stability of the compounds represented by general formula (1) is especially required, $X^1$, $X^2$, $X^3$, and $X^4$ are preferably selected from the group consisting of single bonds, —(CH$_2$)$_2$—, —COO—, —OCO—, —CH$_2$O—, —OCH$_2$—, —(CH$_2$)$_4$—, —(CH$_2$)$_3$O—, —O(CH$_2$)$_3$—, —CF$_2$O—, —OCF$_2$—, —CH$_2$CF$_2$—, —CF$_2$CH$_2$—, —(CF$_2$)$_2$—, —(CF$_2$)$_4$—, —(CH$_2$)$_2$COO—, and —OCO(CH$_2$)$_2$—.

In general formula (1), at least one of rings $A^1$, $A^2$, $A^3$, $A^4$, and $A^5$ is 6,6-difluorotetrahydropyran-2,5-diyl, 6,6-difluoro-2,3-dihydro-6H-pyran-2,5-diyl, or 6-fluromo-3,4-dihydro-2H-pyran-2,5-diyl. Other preferable rings include bicyclo[1.1.1]pentane-1,3-diyl, trans-cyclohexane-1,4-diyl, cyclohexa-1-ene-1,4-diyl, and 1,4-phenylene, in which carbon atoms constituting these rings may be substituted by nitrogen atoms, oxygen atoms, or sulfur atoms, and hydrogen atoms on the ring may be substituted by halogen atoms or cyano groups.

Specifically, these rings include 1-cyano-trans-cyclohexane-1,4-diyl, 2,2-difluoro-trans-cyclohexane-1,4-diyl, 2-fluorocyclohexa-1-ene-1,4-diyl, 2,2-dichlorobicyclo[1.1.1]pentane-1,3-diyl, and 2,3-difluorobenzene-1,4-diyl.

In addition to the above, rings in which hydrogen atoms on the ring may be substituted by fluorine or chlorine atoms or cyano groups are listed below:

Bicyclo[1.1.1.]pentane-1,3-diyl, trans-cyclohexane-1,4-diyl, cyclohexa-1-ene-1,4-diyl, 1,4-phenylene, 1,3-dioxane-2,5-diyl, pyrimidine-2,5-diyl, pyridine-2,5-diyl, pyrazine-2,5-diyl, pyridazine-3,6-diyl, tetrahydropyran-2,5-diyl, 1,3-dithian-2,5-diyl, 1,3-oxathian-2,5-diyl, and bicyclo[2.2.2]octane-i,4-diyl.

When high chemical and physical stability of the compounds represented by general formula (1) is especially required, rings $A^1$, $A^2$, $A^3$, $A^4$, and $A^5$ are preferably selected from the group consisting of 6,6-difluorotetrahydropyran-2,5-diyl, 6,6-difluoro-2,3-dihydro-6H-pyran-2,5-diyl, or 6-fluromo-3,4-dihydro-2H-pyran-2,5-diyl. Other preferable rings used as rings $A^1$, $A^2$, $A^3$, $A^4$ and $A^5$ are listed below:

1-cyano-trans-cyclohexane-1,4-diyl, 2,2-difluoro-trans-cyclohexane-1,4-diyl, 2-fluorocyuclohexa-1-ene-1,4-diyl, 2,2-dichlorobicyclo[1.1.1]pentane-1,3-diyl, and 2,3-difluorobenzene-1,4-diyl.

In addition to the above, rings in which hydrogen atoms on the ring may be substituted by fluorine or chlorine atoms or cyano groups are listed below:

Bicyclo [1.1.1]pentane-1,3-diyl, trans-cyclohexane-1,4-diyl, cyclohexa-1-ene-1,4-diyl, 1,4-phenylene, 1,3-dioxane-2,5-diyl, pyrimidine-2,5-diyl, pyridine-2,5-diyl, pyridazine-3,6-diyl, tetrahydropyran-2,5-diyl, 1,3-dithian-2,5-diyl, and 1,3-oxathian-2,5-diyl.

When a larger absolute value of the negative Δε of the compounds represented by general formula (1) is desired, rings $A^1$, $A^2$, $A^3$, $A^4$, and $A^5$ are preferably selected from the group consisting of 6,6-difluorotetrahydropyran-2,5-diyl, 6,6-difluoro-2,3-dihydro-6H-pyran-2,5-diyl, and 6-fluoro-3,4-dihydro-2H-pyran-2,5-diyl. Other preferable rings used as rings $A^1$, $A^2$, $A^3$, $A^4$, and $A^5$ are listed below:

1-cyano-trans-cyclohexane-1,4-diyl, 2,2-difluoro-trans-cyclohexane- 1,4-diyl, 2-fluorocyclohexa-1-ene-1,4-diyl, 2,2-dichlorobicyclo[1.1.1]pentane-1,3-diyl, and 2,3-difluorobenzene-1,4-diyl.

In addition to the above, rings in which hydrogen atoms on the ring may be substituted by fluorine or chlorine atoms or cyano groups are listed below:

Trans-cyclohexane-1,4-diyl, clohexa-1-ene-1,4-diyl, pyridazine-3,6-diyl, and tetrahydropyran-2,5-diyl.

The compounds of the present invention according to claim 1 or 2 have large absolute values of negative Δε. Therefore, by use of mainly the compounds of the present invention, liquid crystal compositions having negative Δε can be prepared. Such liquid crystal compositions are useful for fabricating liquid crystal display elements from liquid crystal compositions having negative Δε, particularly those of the vertical orientation system as described in Japanese Patent Application Laid-open No. 2-176625, or IPS. Since mixing a compound of the present invention with other liquid crystal compounds or compositions enables proper adjustment of the Δε, the scope of application of other liquid crystal compounds or compositions can be expanded.

The compounds of the present invention according to claim 1 or 2 have small elastic coefficients, and the temperature dependence of these coefficients is small. Therefore, a novel liquid crystal composition of a low operating voltage can be prepared from the compounds of the present invention.

The compounds of the present invention according to claim 1 or 2 are highly miscible with other liquid crystalline compounds. Therefore, when the compounds of the present invention are blended with other liquid crystal compositions, there seldom arise problems such as precipitation of the compounds. Also, the compounds of the present invention can be used in a liquid crystal composition in large quantities, reflecting their excellent properties.

The Δn of the compounds of the present invention according to claim 1 or 2 can be adjusted to desired values by proper design of their structures. That is, if an especially high Δn is desired, there may be selected rings containing a large number of sites having resonance structures, such as aromatic rings. If a low Δn is desired, there may be selected rings containing a large number of sites having no resonance structures, such as trans-cyclohexane-1,4-diyl rings.

Specifically, the Δn of the compounds of the present invention represented by general formula (1) can be adjusted to desired values by proper selection of $R^1$, $Y^1$, $X^1$, $X^2$, $X^3$, $X^4$, ring $A^1$, ring $A^2$, ring $A^3$, ring $A^4$, ring $A^5$, l, m, n, o, and p. More specifically, Δn can be adjusted by proper selection of ring $A^1$, ring $A^2$, ring $A^3$, ring $A^4$, and ring $A^5$. That is, if an especially high Δn is desired, there may be selected rings containing a large number of sites having resonance structures, such as aromatic rings. If a low Δn is desired, there may be selected rings containing a large number of sites having no resonance structures, such as trans-cyclohexane-1,4-diyl rings.

By the free selection of Δn, the degree of freedom of liquid crystal display panel design will increase.

Compounds of the present invention according to claim 1 or 2 have low viscosity, and even if the compounds are used in large quantities in a liquid crystal composition, they will not significantly increase the viscosity of the overall liquid crystal composition. The temperature dependence of viscosity, in particular that at low temperature, is extremely small. By the use of liquid crystalline compounds of the present invention having excellent viscosity, a liquid crystal composition having a short response time can be prepared.

Compounds of the present invention according to claim 1 or 2 are chemically and physically stable, and a liquid crystal composition prepared from such compounds has a high specific resistance and voltage holding ratio. The compounds have high stability against external factors such as ultraviolet radiation and heat, which is a sufficient requirement for obtaining practical liquid crystal compositions.

The phase-transfer temperature of the compounds of the present invention according to claim 1 or 2 can be adjusted by proper selection of the number of rings. That is, when an especially high clearing point is required, a compound having 4 rings may be selected; when a moderate clearing point is required, a compound having 3 rings may be selected; and when an especially low clearing point is required, a compound having 2 rings may be selected.

More specifically, the phase-transfer temperature of the present invention represented by the general formula (1) can be adjusted by proper selection of the values of l, m, n, o, and p. That is, when an especially high clearing point is required, a compound having 4 or more rings with l+m+n+o+p≧4 may be selected; when a moderate clearing point is required, a compound having 3 rings with l+m+n+o+p=3 may be selected; when an especially low clearing point is required, a compound having 2 rings with l+m+n+o+p=2 may be selected.

As described above, the compounds of the present invention according to claim 1 or 2 have favorable properties as materials for electro-optical displays. A novel liquid crystal composition having excellent properties can be prepared from the compounds of the present invention. Also, by proper design of the structures according to uses, a liquid crystalline compound having desired properties can be prepared, and a liquid crystal composition and a liquid crystal display element can be obtained from such a compound.

Although the compounds of the present invention feature large negative Δε, the compounds can be used not only in liquid crystal compositions having negative Δε, but also for addition to liquid crystal compositions having positive, Δε so as to adjust their Δε or other properties.

More specifically, the compounds of the present invention or the liquid crystal compositions prepared from such compounds can be used in various display systems using compounds or compositions having negative Δε (for example, the homeotropic orientation system as disclosed in Japanese Patent Application Laid-open No. 2-176625, IPS, ECB (HAN or DAP), DS, GH, or PC), particularly in the homeotropic orientation system as disclosed in Japanese Patent Application Laid-open No. 2-176625 and IPS. Such compounds can be used not only in these systems, but also for improving or adjusting various properties (for example, Δε, elastic coefficients, Δn, viscosity, or chemical and physical stability) of liquid crystal compositions for various display systems using compounds or compositions having positive Δε (for example, TN, STN, or TN-based AM (TFT or MIM)).

The liquid crystal composition of the present invention will now be described. The liquid crystal composition according to the present invention preferably contains at least one of the compounds described in claim 1 or 2 in an amount of 0.1 to 99.9 percent by weight for exhibiting excellent properties.

More specifically, the liquid crystal composition provided by the present invention comprises the first component containing at least one of the compounds described in claim 1 or 2 to which are added compounds selected from the group consisting of general formulas (2) through (12), in adequate amounts according to the purpose of the liquid crystal composition.

Preferred compounds used in the liquid crystal composition of the present invention represented by general formulas (2) through (4) are listed below. (In these formulas, $R^2$ and $Y^2$ have the same meanings as defined previously.)

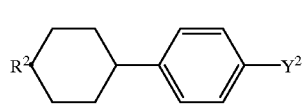

(2-1)

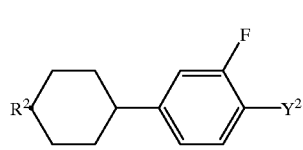

(2-2)

(2-3) 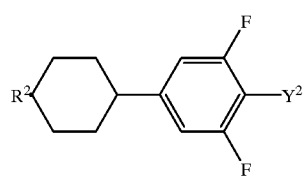
(2-4) 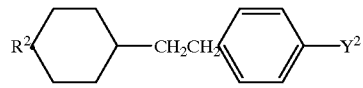
(2-5) 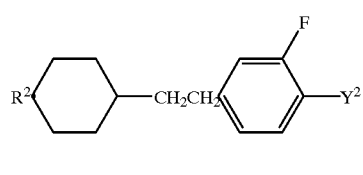
(2-6) 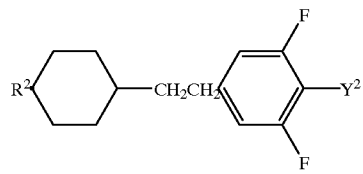
(2-7) 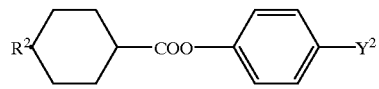
(2-8) 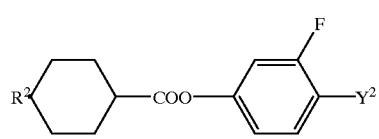
(2-9) 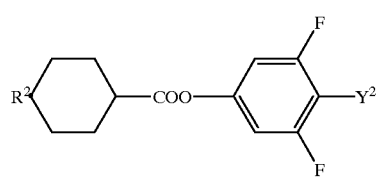
(3-1) 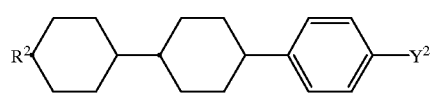
(3-2) 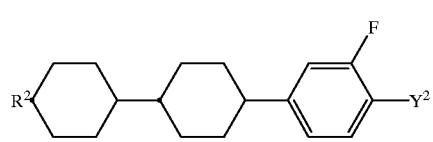
(3-3) 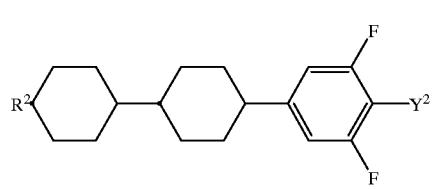
(3-4) 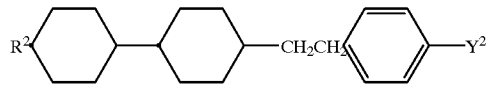
(3-5) 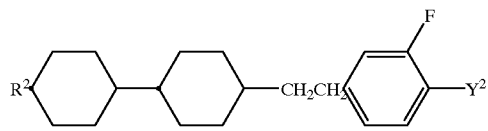
(3-6) 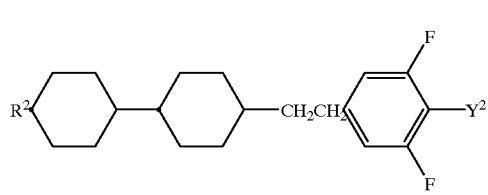
(3-7) 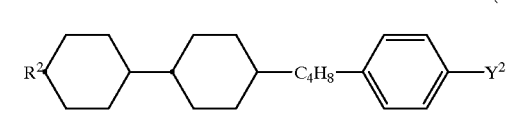
(3-8) 
(3-9) 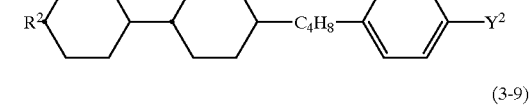
(3-10) 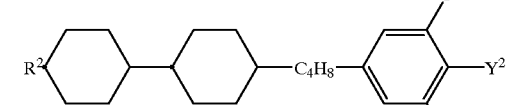
(3-11) 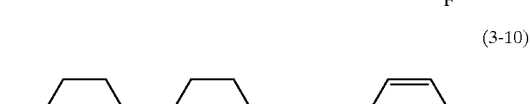
(3-12) 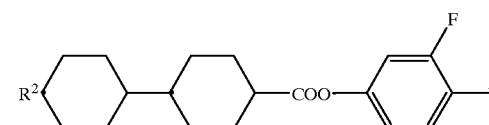

(3-13) 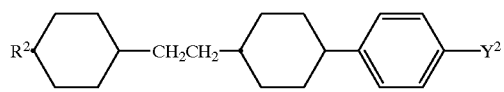
(3-14) 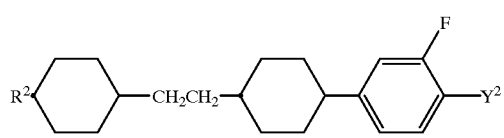
(3-15) 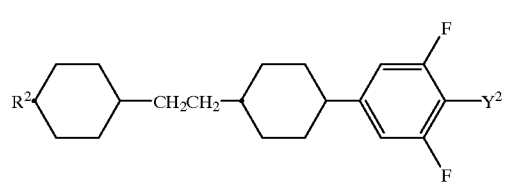
(3-16) 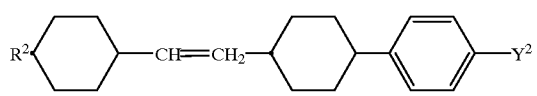
(3-17) 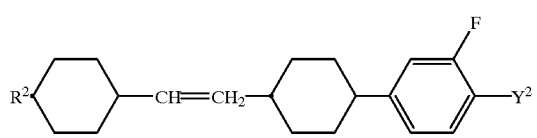
(3-18) 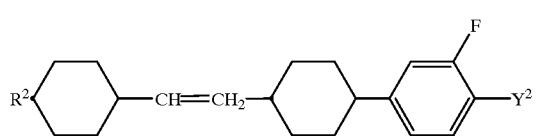
(3-19) 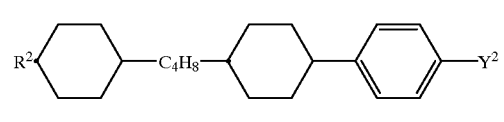
(3-20) 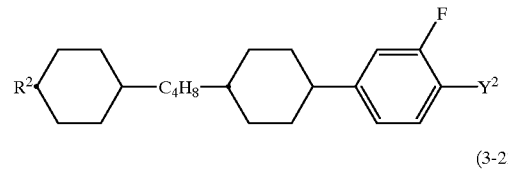
(3-21) 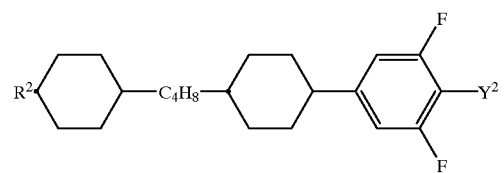
(3-22) 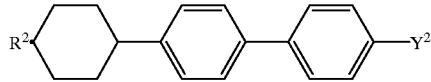
(3-23) 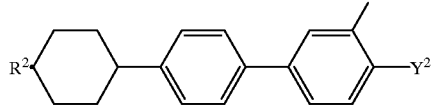
(3-24) 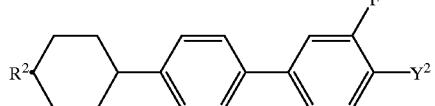
(3-25) 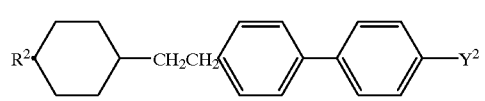
(3-26) 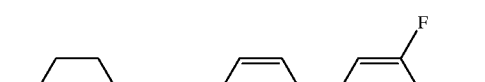
(3-27) 
(3-28) 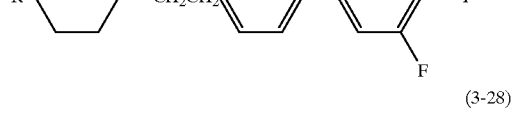
(3-29) 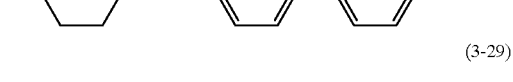
(3-30) 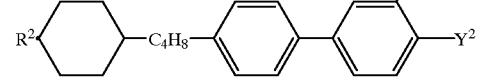
(3-31) 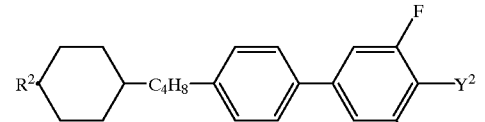

(3-32) 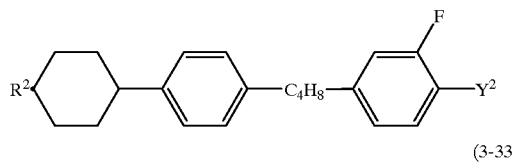
(3-33) 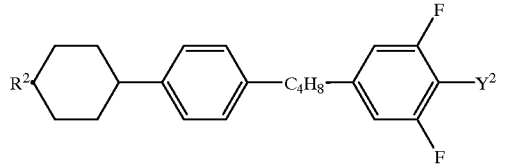
(3-34) 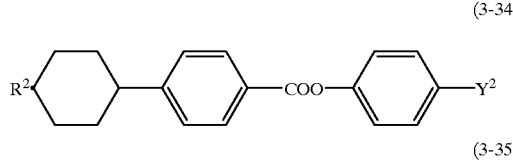
(3-35) 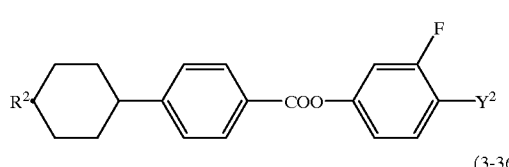
(3-36) 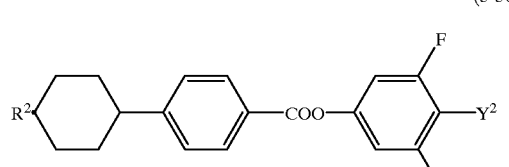
(3-37) 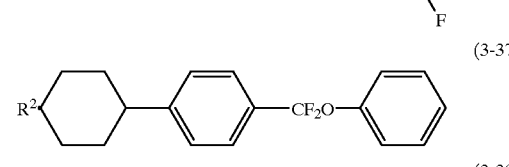
(3-38) 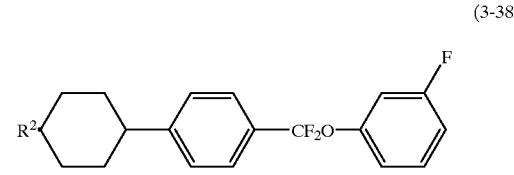
(3-39) 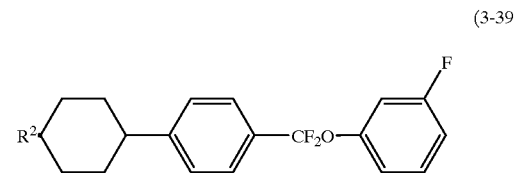
(3-40) 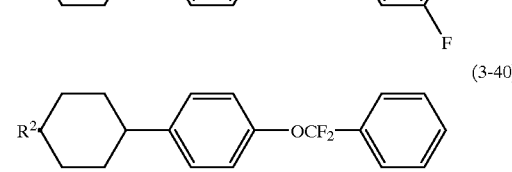
(3-41)
(3-42) 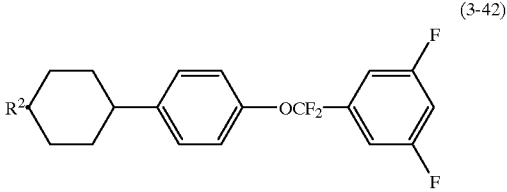
(3-43) 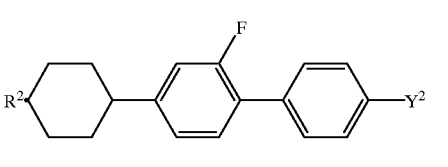
(3-44) 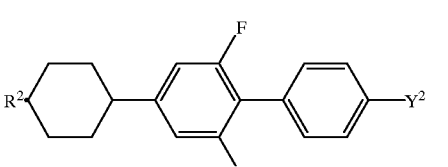
(3-45) 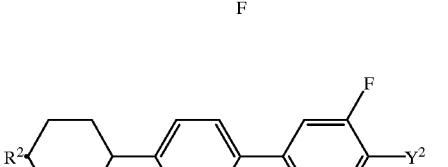
(3-46) 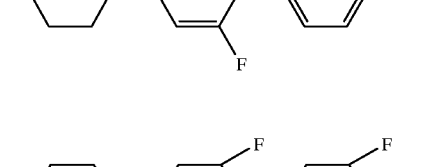
(3-47) 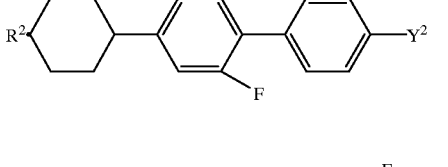
(3-48) 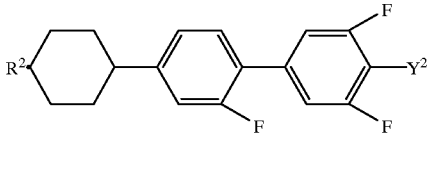
(3-49) 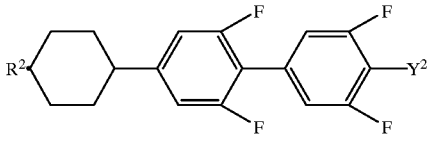
(3-50) 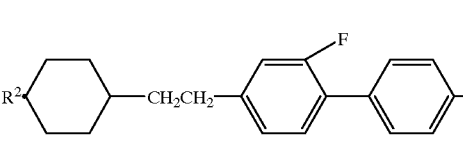
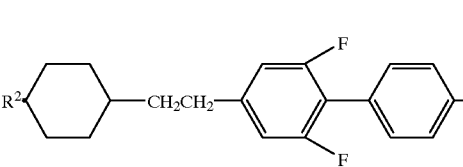

(3-51) 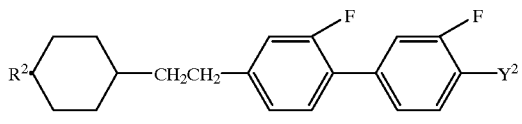
(3-52) 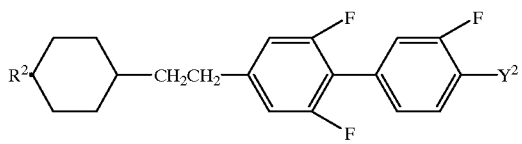
(3-53) 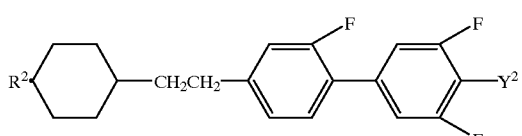
(3-54) 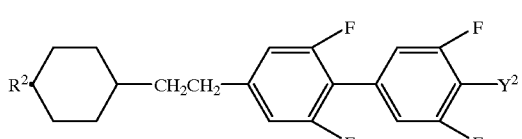
(3-55) 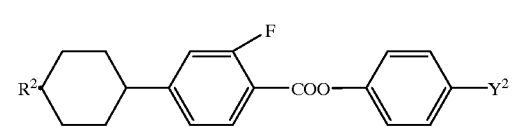
(3-56) 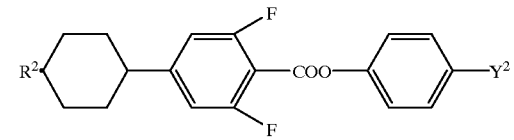
(3-57) 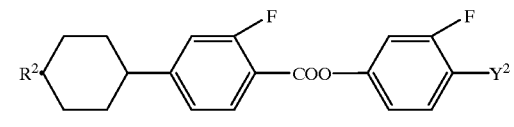
(3-58) 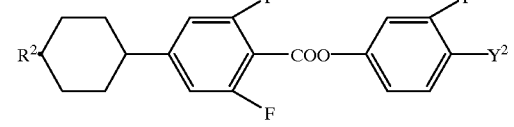
(3-59) 
(3-60) 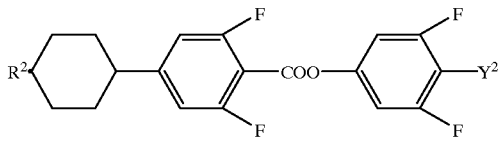
(3-61) 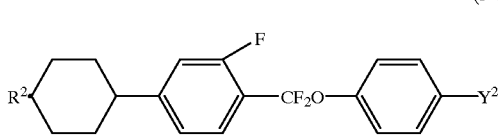
(3-62) 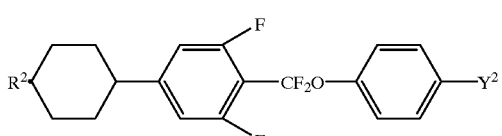
(3-63) 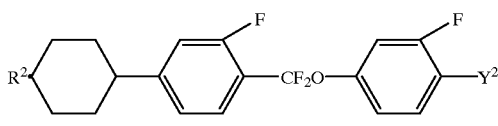
(3-64) 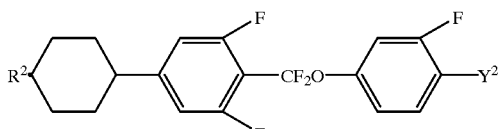
(3-65) 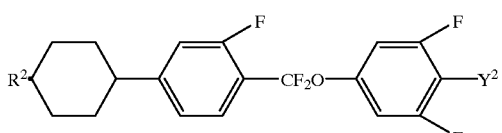
(3-66) 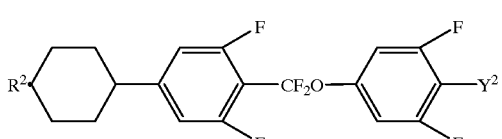
(3-67) 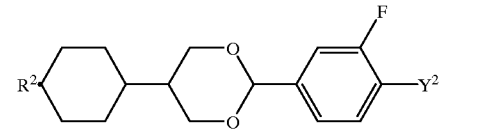
(3-69) 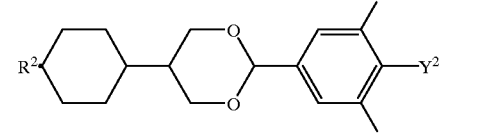

-continued
(4-1)
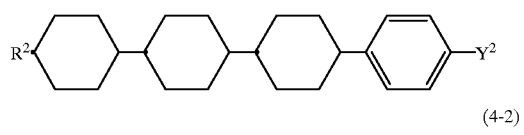
(4-2)
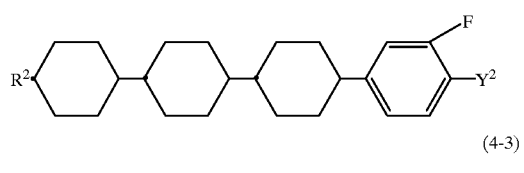
(4-3)
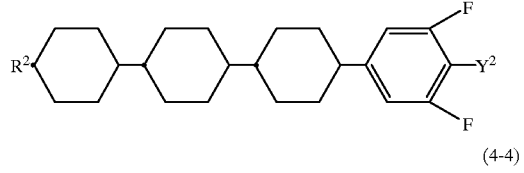
(4-4)
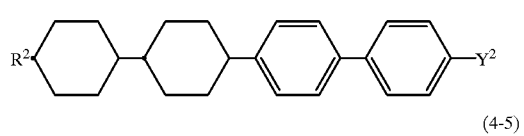
(4-5)
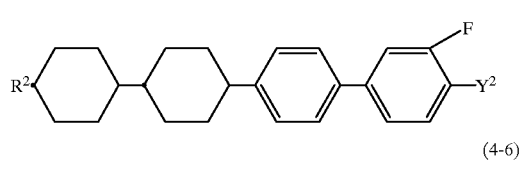
(4-6)
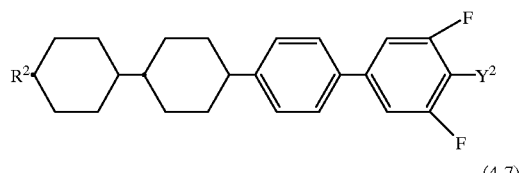
(4-7)
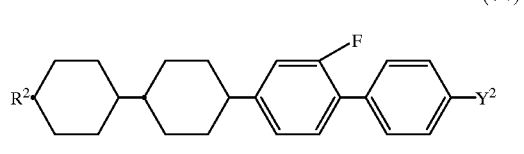
(4-8)
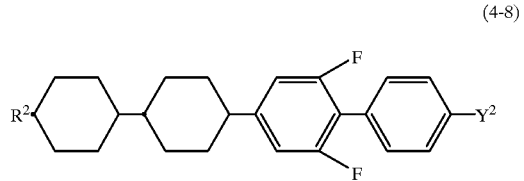
(4-8)
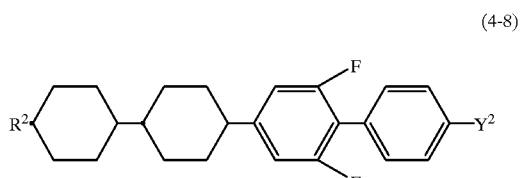
(4-9)
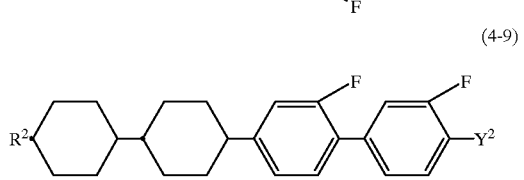
-continued
(4-10)
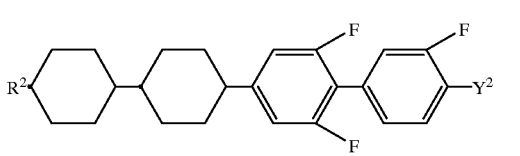
(4-11)
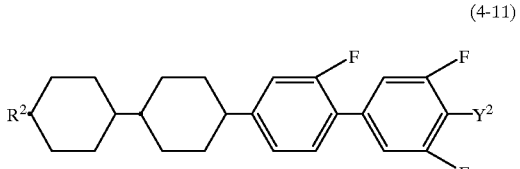
(4-12)
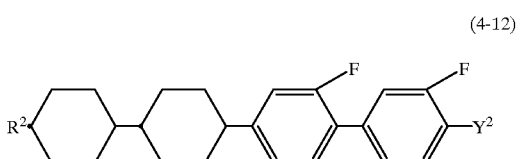
(4-13)
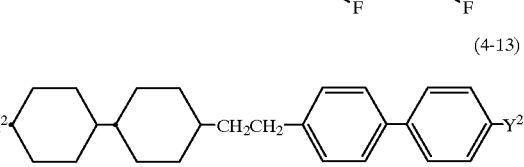
(4-14)
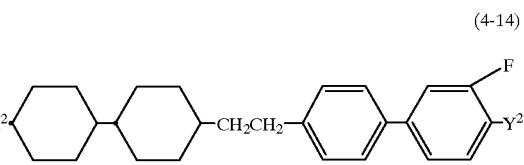
(4-15)
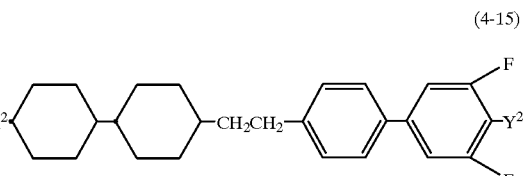
(4-16)
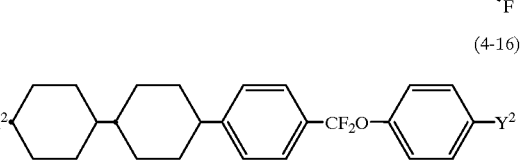
(4-17)
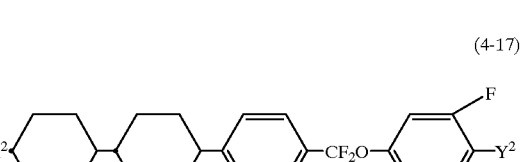
(4-18)
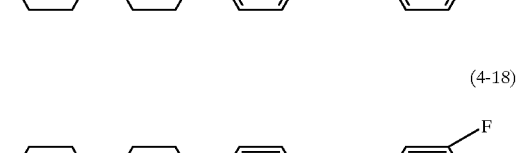
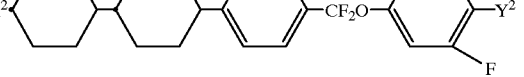

-continued (4-18)
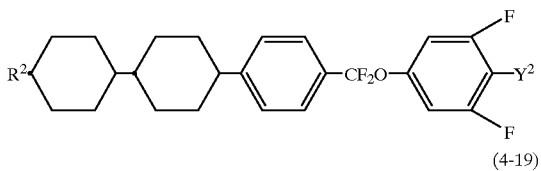

(4-19)
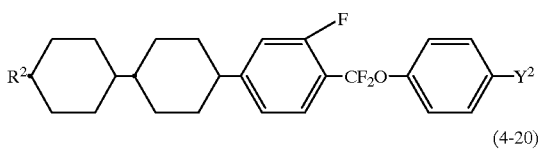

(4-20)
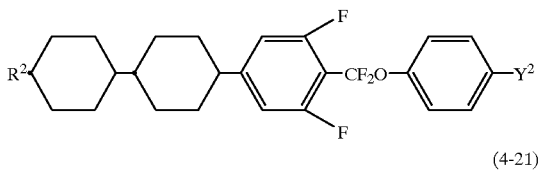

(4-21)
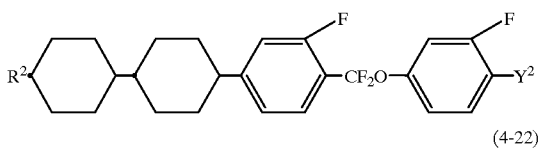

(4-22)
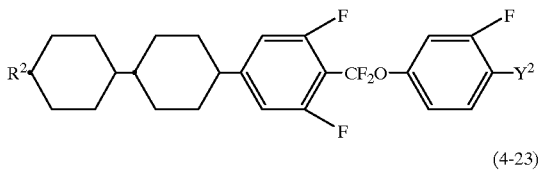

(4-23)
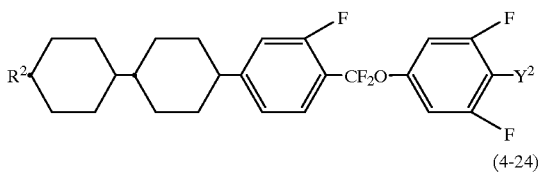

(4-24)
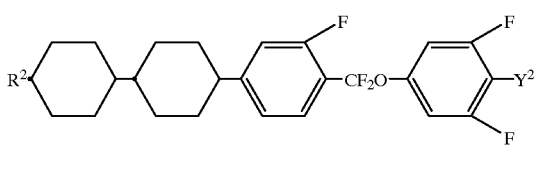

The compounds represented by general formulas (2) through (4) have positive Δε, excellent thermal and chemical stability, and are especially preferred for preparing liquid crystal compositions for TFT displays which require high reliability, i.e. high voltage holding ratio and high specific resistance.

For the preparation of liquid crystal compositions for TFT displays, the quantities of the compounds represented by general formulas (2) through (4) may be within the range of 0.1 to 99.9 percent by weight, preferably 10 to 97 percent by weight, and more preferably 40 to 95 percent by weight relative to the total weight of the liquid crystal composition. The compounds represented by general formulas (7) through (9) may further be contained for adjustment of viscosity.

The compounds represented by general formulas (2) through (4) may also be used for the preparation of liquid crystal compositions for STN and TN displays. In these cases, the compounds are preferably contained in amounts of 50 percent by weight or less.

Preferred compounds used in the liquid crystal compositions of the present invention represented by general formulas (5) and (6) are listed below. (In these formulas, $R^3$, $Y^3$, and $R^4$ have the same meanings as defined previously.)

(5-1)
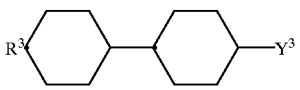

(5-2)
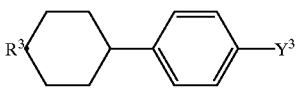

(5-3)
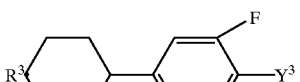

(5-4)
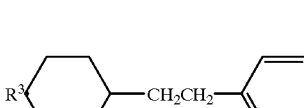

(5-5)
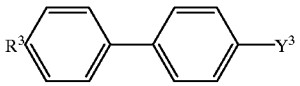

(5-6)
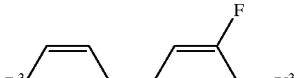

(5-7)
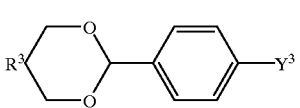

(5-8)
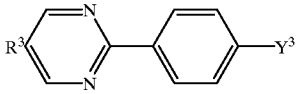

(5-9)
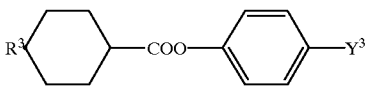

(5-10)
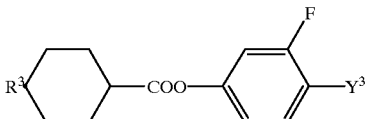

(5-11)

(5-12) 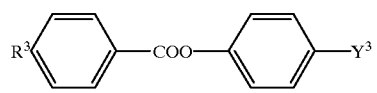
(5-13) 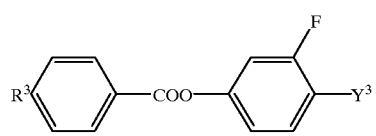
(5-14) 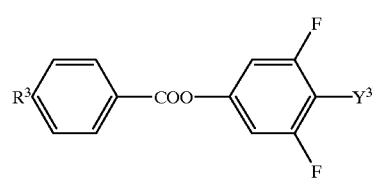
(5-15) 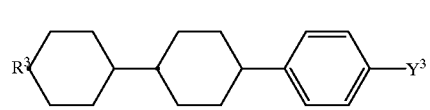
(5-16) 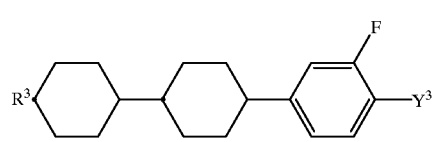
(5-17) 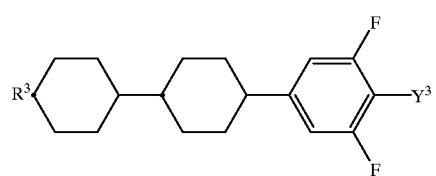
(5-18) 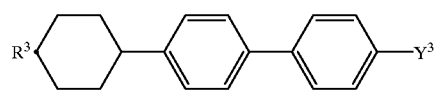
(5-19) 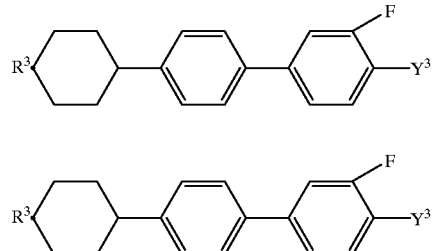
(5-20) 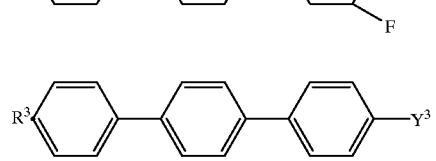
(5-21) 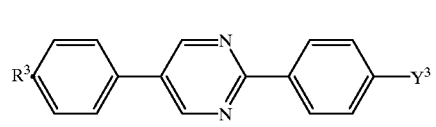
(5-22) 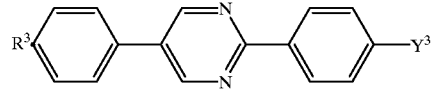
(5-23) 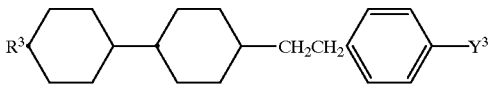
(5-24) 
(5-25) 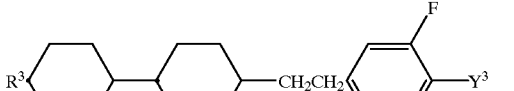
(5-26) 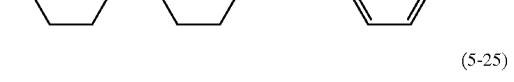
(5-27) 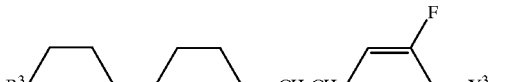
(5-28) 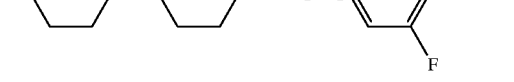
(5-29) 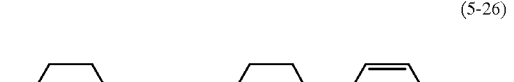
(5-30) 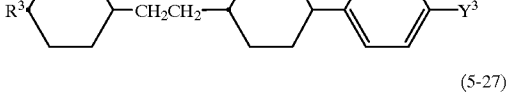

(5-31)
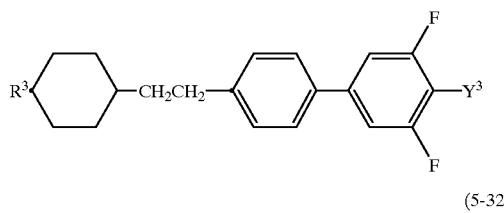

(5-32)
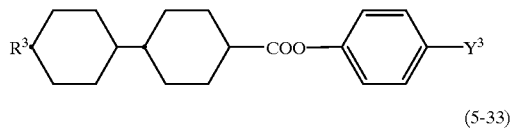

(5-33)
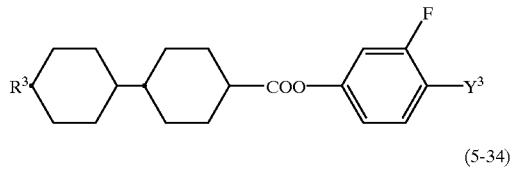

(5-34)
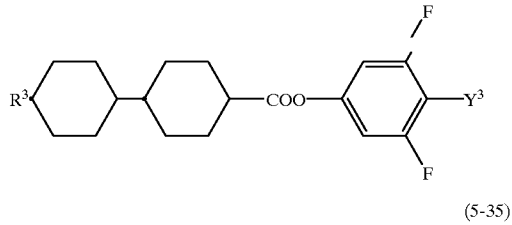

(5-35)
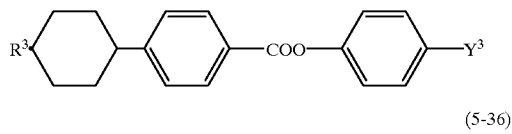

(5-36)
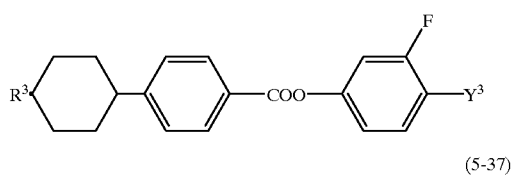

(5-37)
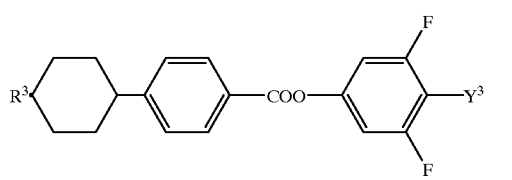

(5-38)
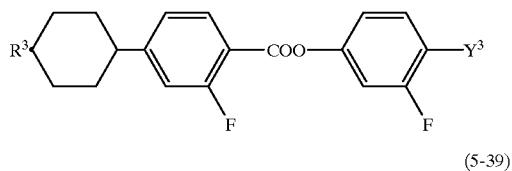

(5-39)
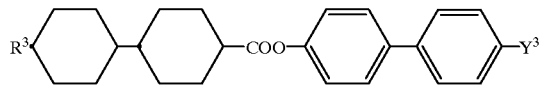

(5-40)
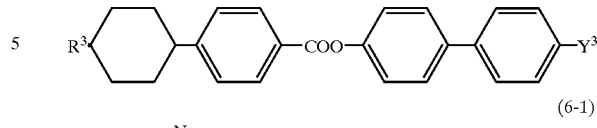

(6-1)
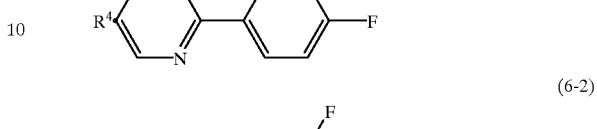

(6-2)
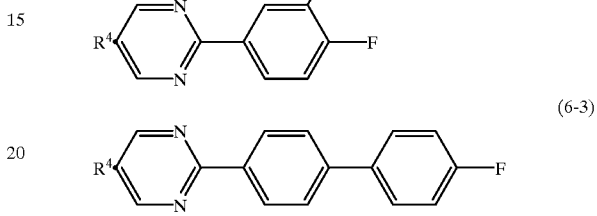

(6-3)

The compounds represented by general formulas (5) and (6) have positive $\Delta\epsilon$, and are used especially for lowering the threshold voltage of the liquid crystal composition. These compounds are also used for adjusting $\Delta n$ values and expanding the nematic range through, for example, raising clearing points. Furthermore, these compounds are used for improving the sharpness of the V-T curve of liquid crystal compositions for STN and TN displays.

The compounds represented by general formulas (5) and (6) are especially preferred for preparing liquid crystal compositions for STN and TN displays.

Increase in the quantity of the compounds represented by general formulas (5) and (6) lowers the threshold voltage and increases the viscosity of the liquid crystal composition. Therefore, so long as the viscosity of the liquid crystal composition satisfies requirements, use of such compounds in large quantities is advantageous for low-voltage operation. The quantity of the compounds represented by general formulas (5) and (6) used for preparing liquid crystal compositions for STN and TN displays may be within the range of 0.1 to 99.9 percent by weight, and are preferably 10 to 97 percent by weight, more preferably 40 to 95 percent by weight.

Preferred compounds used in the liquid crystal composition of the present invention represented by general formulas (7) through (9) are listed below. (In these formulas, $R^5$ and $R^6$ have the same meanings as defined previously.)

(7-1)
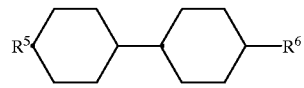

(7-2)
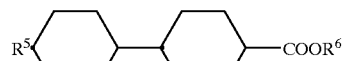

(7-3)
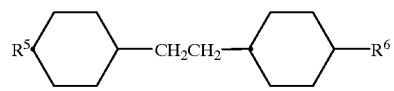

(7-4) 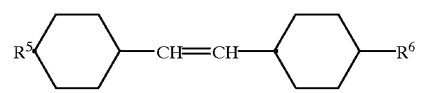
(7-5) 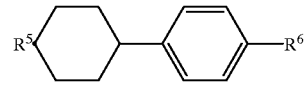
(7-6) 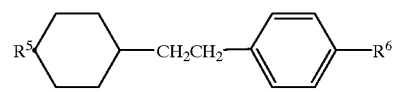
(7-7) 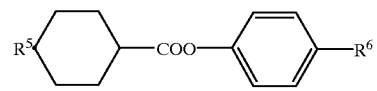
(7-8) 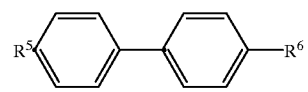
(7-9) 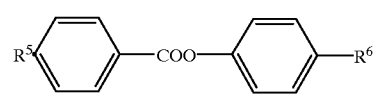
(7-10) 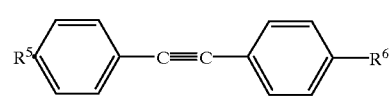
(7-11) 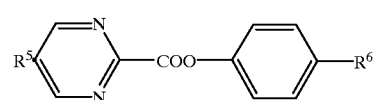
(8-1) 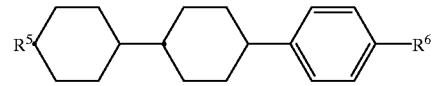
(8-2) 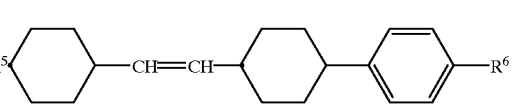
(8-3) 
(8-4) 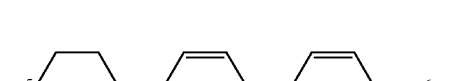
(8-5) 
(8-6) 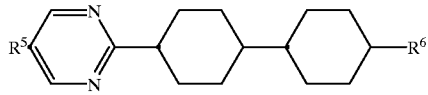
(8-7) 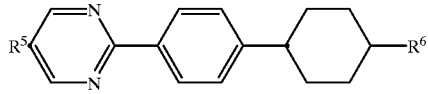
(8-8) 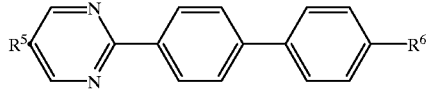
(8-9) 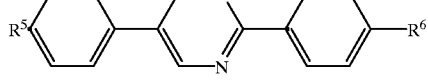
(8-10) 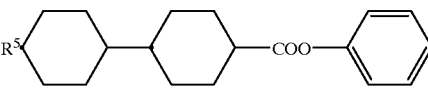
(8-11) 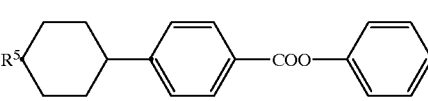
(8-12) 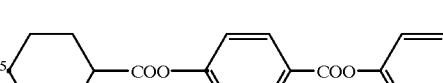
(8-13) 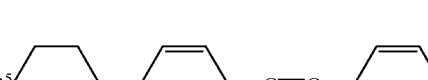
(8-14) 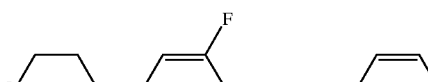
(8-15) 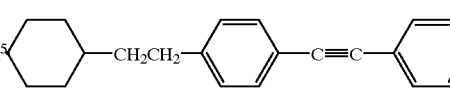
(8-16) 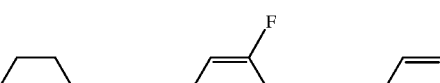
(8-17) 

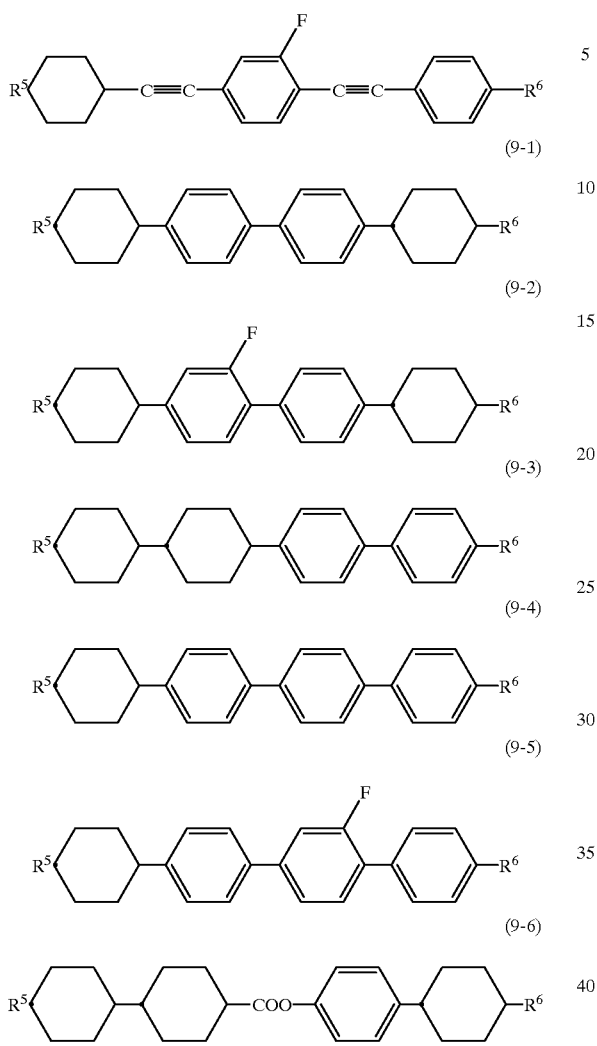

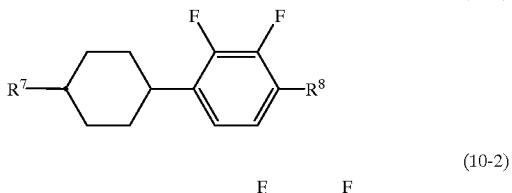

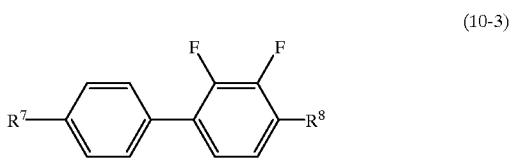

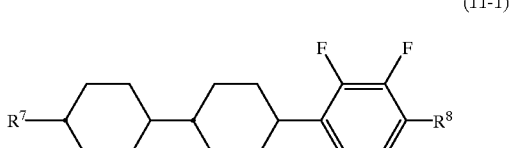

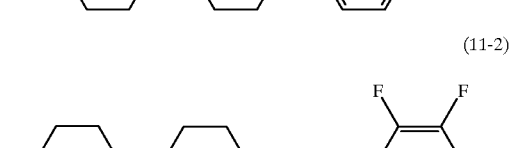

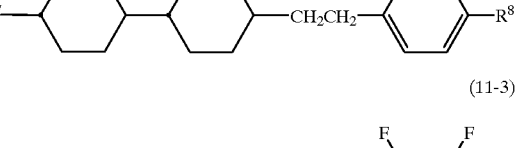

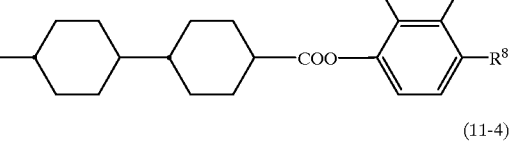

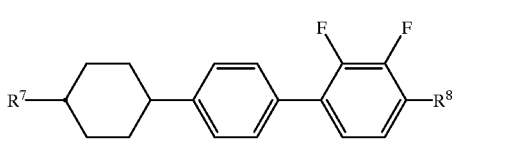

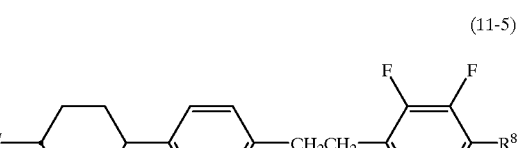

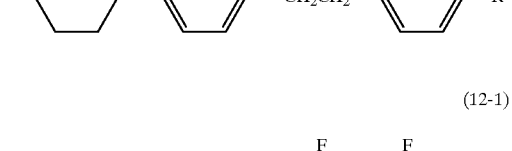

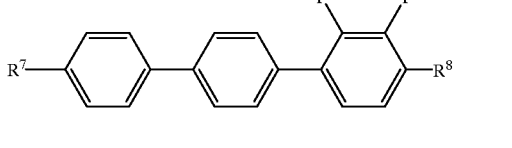

The compounds represented by general formulas (7) through (9) have small absolute values of $\Delta\epsilon$, and are nearly neutral. The compounds represented by general formulas (7) are mainly used for adjusting viscosity and $\Delta\epsilon$. The compounds represented by general formulas (8) and (9) are used for expanding the nematic range through, for example, raising clearing points or adjusting $\Delta n$.

Increase in the quantity of the compounds represented by general formulas (7) through (9) increases the viscosity and lowers the threshold voltage of the liquid crystal composition. Therefore, so long as the threshold voltage of the liquid crystal composition satisfies requirements, use of the compounds in large quantities is preferred. The quantities of the compounds represented by general formulas (7) through (9) are preferably 40 percent by weight or less, more preferably 35 percent by weight or less. The quantities for preparing liquid crystal compositions for STN or TN displays are preferably 70 percent by weight or less, more preferably 60 percent by weight or less.

Preferred compounds used in the liquid crystal composition of the present invention represented by general formulas (10) through (12) are listed below. (In these formulas, $R^7$ and $R^8$ have the same meanings as defined previously.)

(12-2)

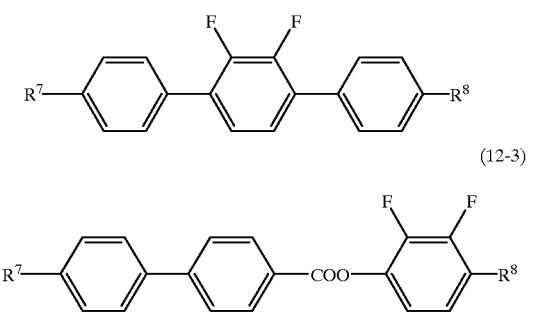

(12-3)

Like the compounds according to claim 1 or 2, the compounds represented by general formulas (10) through (12) have negative Δε, and are used for the bases of N-type liquid crystal compositions or for controlling the Δε of P-type liquid crystal compositions.

Other main uses of the compounds having two rings represented by general formula (10) include the adjustment of threshold voltages, viscosity, or Δn. The compounds represented by general formula (11) are used for expanding the nematic range through, for example, raising clearing points or adjusting Δn values. The compounds represented by general formula (12) are used for expanding the nematic range, as well as for lowering threshold voltages and for increasing Δn.

The compounds represented by general formulas (10) through (12) are mainly used for preparing N-type liquid crystal compositions. Increase in their quantities lowers the threshold voltages and increases the viscosity of the liquid crystal compositions. Therefore, so long as the threshold voltage of the liquid crystal composition satisfies requirements, use of the compounds in small quantities is preferred. However, since the absolute value of negative Δε is 5 or less, low-voltage operation may become difficult if the quantities are less than 40 percent by weight. When a liquid crystal composition for preparing liquid crystal compositions for N-type TFT displays is to be obtained, the preferred quantity of the compounds represented by general formulas (10) through (12) is 40 percent by weight or more, and more preferably 50 to 95 percent by weight. The compounds represented by general formulas (10) through (12) may also be mixed with P-type compositions for controlling the elastic coefficient and controlling the voltage-transmittance curve (V-T curve) of the liquid crystal composition. In this case, the quantity of the compounds represented by general formulas (10) through (12) is preferably 30 percent by weight or less.

Except in special cases such as the liquid crystal compositions for OCB (optically compensated birefringence), an optically active compound is normally added to the liquid crystal composition of the present invention for adjusting required twist angle by inducing formation of the helical structure of the liquid crystal composition, and for preventing reverse twist.

Although any known optically active compounds used for the above purposes may be used in the present invention, preferred compounds include the following optically active compounds.

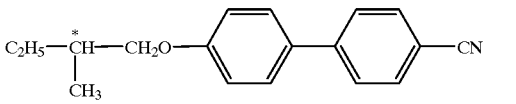

C15

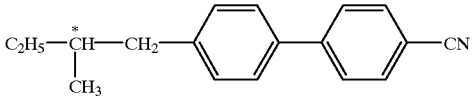

CB15

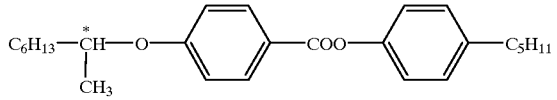

CM21

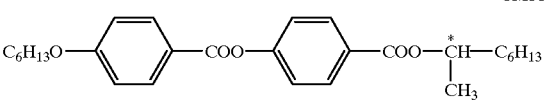

CM33

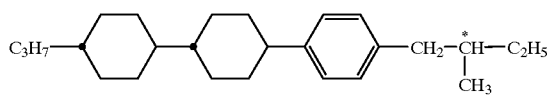

CM44

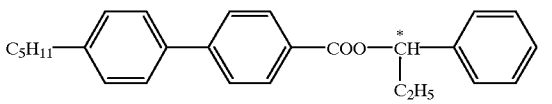

CM45

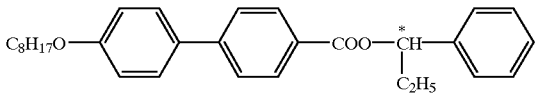

CM47

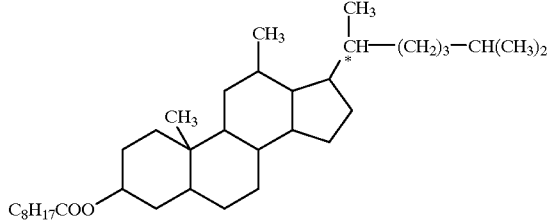

CN

In the liquid crystal compositions of the present invention, the pitch of twist is adjusted by addition of these optically active compounds. The pitch of twist is preferably adjusted within the range of 40 to 200 μm for liquid crystal compositions for TFT and TN displays, 6 to 20 μm for liquid crystal compositions for STN displays, and 1.5 to 4 μm for liquid crystal compositions for bistable TN displays. For adjustment of the temperature dependence of the pitch, two or more optically active compounds may be added.

The liquid crystal composition of the present invention can also be used as a GH-mode liquid crystal composition by the addition of merocyanine, styryl, azo, azomethine, azoxy, quinophthalone, anthraquinone, and tetrazine dichroic pigments. It can also be used as the liquid crystal composition for polymer dispersed liquid crystal display (PDLCD) elements, represented by NCAPs produced from the microcapsules of nematic liquid crystals, or polymer network liquid crystal display (PNLCD) elements produced by incorporation of three-dimensional matrices of polymers in the liquid crystals. Other uses include liquid crystal compositions for the DS mode.

The liquid crystal composition of the present invention is prepared by methods well known to those skilled in the art. In general, a method in which various components are dissolved in each other at high temperature is used.

The compound of the present invention according to claim 1 or 2 can be prepared easily by known chemical methods for synthesizing organic compounds. An example preparation method is shown by reaction formula 1.

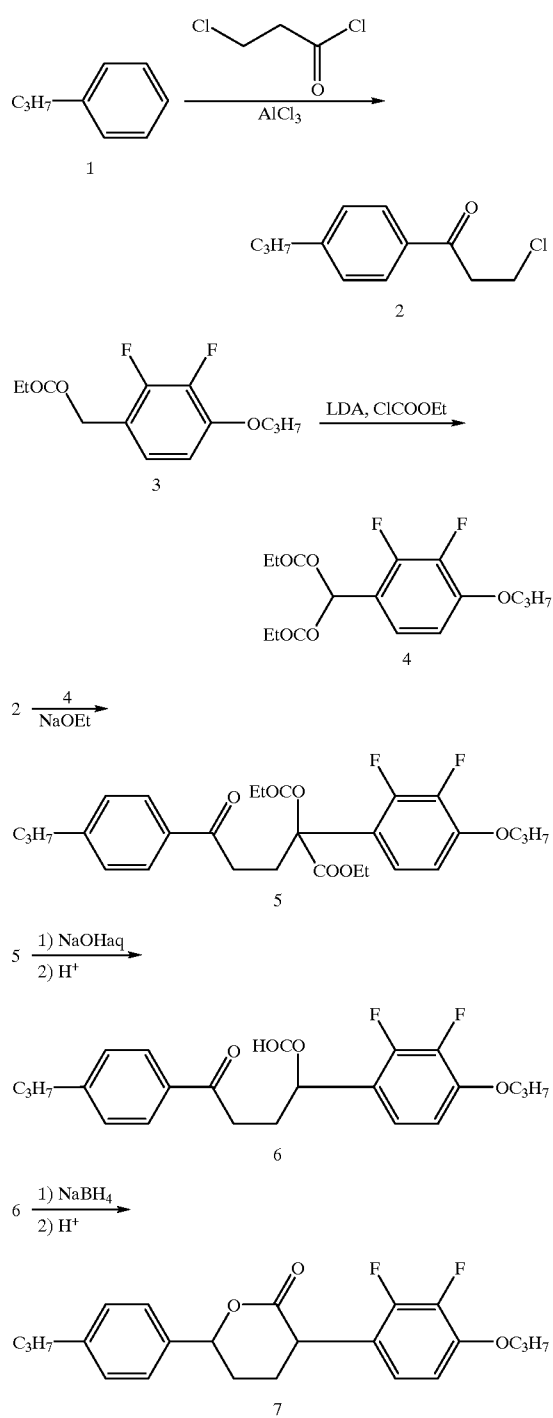

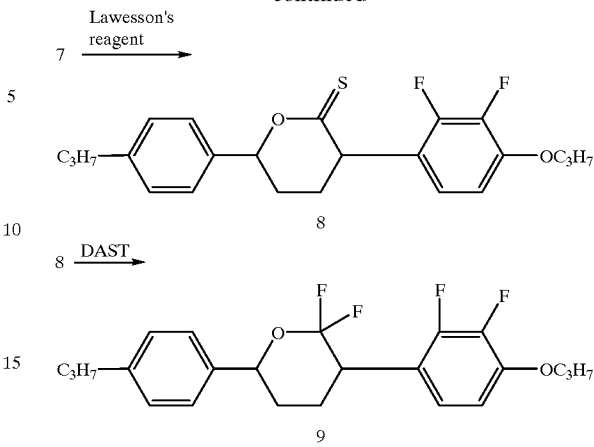

The above synthesizing method will be described below.

To the compound of formula 1, 3-chloropropionly chloride is added by a Friedel-Crafts reaction in the presence of aluminum chloride to derive the compound of formula 2.

The compound of formula 3 is allowed to react with ethyl chloroformate in the presence of lithium diisopropylamide (LDA) to derive the compound of formula 4.

The compound of formula 2 is allowed to react with the compound of formula 4 in the presence of NaOEt to derive the compound of formula 5, which is hydrolyzed by NaOH to derive a ketocarbonic acid of formula 6. This is reduced by sodium borohydride (SBH) to derive a lactone compound of formula 7, which is converted to a thiolactone compound of formula 8 by Lawesson's reagent (2,4-bis(4-methoxyphenyl)-1,3-dithia-2,4-diphosphoethane-2,4-disulfide). Finally, the thiocarbonyl group of the compound of formula 8 is fluorinated by $Et_2NSF_3$ (DAST) to derive the desired compound represented by formula 9.

Compounds represented by general formula (1) may also be synthesized by the following method. Method for synthesizing compounds represented by general formula (1) wherein ring A5 is 6,6-difluorotetrahydropyran-2,5-diyl and p=1 (In the following reaction formulas, $R^x$ represents $R^1-(A^1-X^1)_l-(A^2-X^2)_m-(A^3-X^3)_n-(A^4-X^4)_o-$ in general formula (1) and X represents a halogen.)

Grignard reagent prepared from 2,2-(2-bromoethyl)-1,3-dioxane and magnesium is allowed to react with an aldehyde (X-1), to form an alcohol (X-2). The alcohol (X-2) is oxidized through use of a method such as Swern oxidation or PCC oxidation to form a ketone (X-3). The ketone (X-3) is deprotected by an acid, and $ClCF_2COONa$ is allowed to react with the formed aldehyde (X-4) to form a difluoroolefin (X-5). The difluoroolefin (X-5) is reduced by a reductant such as sodium borohydride (SBH) to form an alcohol (X-6). A halogen is allowed to react with the alcohol (X-6) through use of the method described in Chem. Pharm. Bull. 33 (11) 5144–5146 (1985), to form a compound (X-7) having a 6,6-difluorotetrahydropyran ring wherein $Y^1$ is a halogen atom. Tributyl tin hydrin is allowed to react with the compound (X-7) to form a compound (X-8) having a 6,6-difluorotetrahydropyran ring wherein $Y^1$ is hydrogen atom.

The compound wherein $Y^1$ is an allyl radical is formed by allowing zinc to react with the compound (X-7) by the method described in SYNLETT, 1998, 379–380, and sequentially allowing copper cyanide, lithium chloride, and an allyl bromide to react with the reaction product.

The compound wherein $Y^1$ is a radical other than a halogen atom is formed by allowing dibromodifluoromethane and hexamethyl phosphoric triamide to react with a ketone (X-9) to form a reaction product (X-10), allowing Grignard reagent (X-11) prepared from (X-10) to react with the alcohol (X-1) to form an alcohol (X-12), and forming compounds (X-13) and (X-14) in the same manner as the compound (X-8) is formed from the alcohol (X-6) as described above.

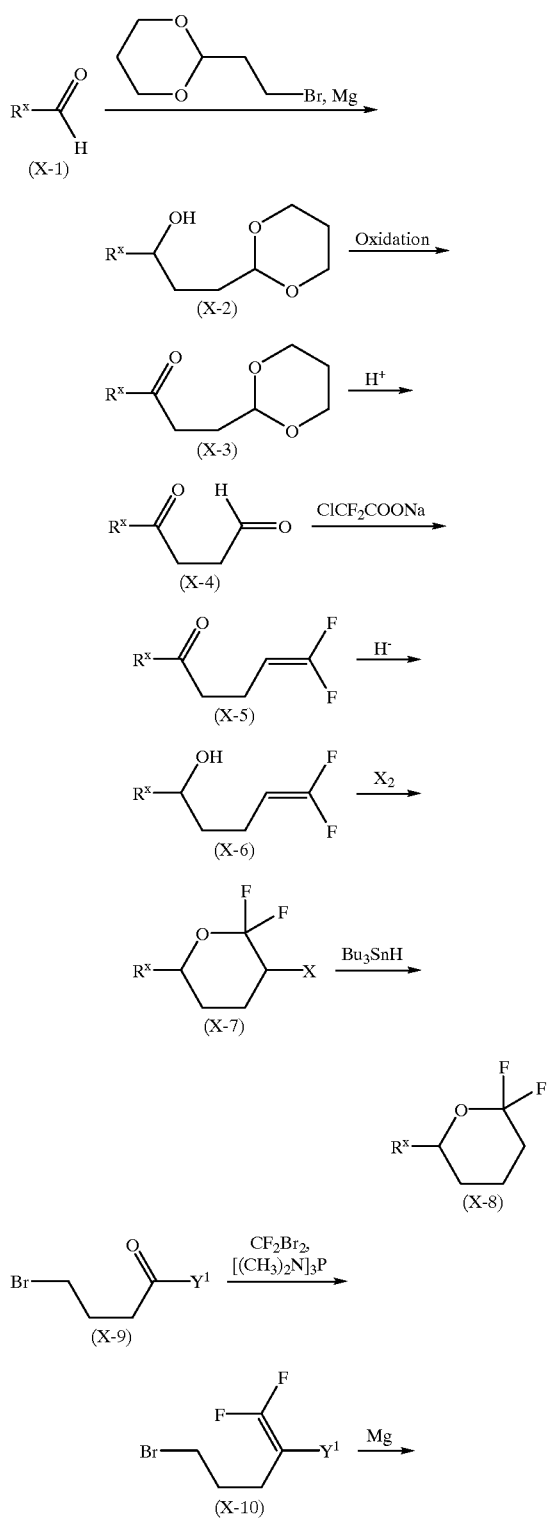

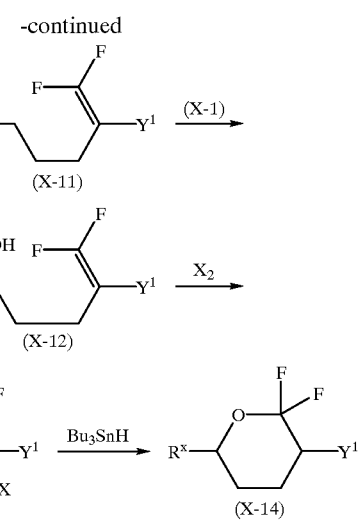

PREFERRED EMBODIMENTS OF THE INVENTION

The method for preparing the compounds of the present invention and examples of their uses will be described in further detail with reference to preferred embodiments. However, the present invention is by no means restricted by these embodiments. In the following description of the embodiments, N represents normality (gram equivalent/liter), M represents molar concentration (mole/liter), Δε represents the value of dielectric anisotropy extrapolated from the value of the composition consisting of 85 percent by weight of the following mother licuid crystal composition A and 15 percent by weight of a compound of the present invention (measured at 25° C.), and Δn represents the measured value of optical anisotropy of the composition consisting of 85 percent by weight of the following mother liquid crystal composition B and 15 percent by weight of a compound of the present invention (measured at 25° C.). Preparation of mother liquid crystal composition A

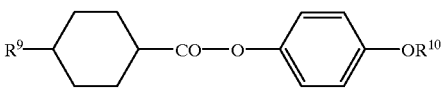

Five ester compounds represented by the above general formula, each having an alkyl group $R^9$ at an end and an alkyl group $R^{10}$ different from the alkyl group $R^9$, were mixed in the following proportions to prepare the mother liquid crystal composition A.

|  | wt. % |
|---|---|
| $R^9 = C_3H_7$, $R^{10} = C_4H_9$ | 27.6 |
| $R^9 = C_4H_9$, $R^{10} = C_2H_5$ | 20.7 |
| $R^9 = C_5H_{11}$, $R^{10} = CH_3$ | 20.7 |
| $R^9 = C_3H_7$, $R^{10} = C_2H_5$ | 17.2 |
| $R^9 = C_5H_{11}$, $R^{10} = C_2H_5$ | 13.8 |
|  | 100.0 |

Δε=1.5

Preparation of mother liquid crystal composition B

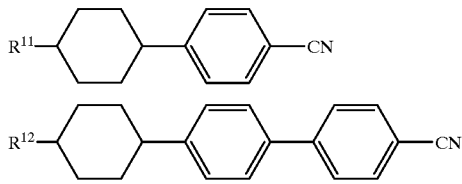

Four compounds represented by the above general formula having different alkyl groups ($R^{11}$ and $R^{12}$) were mixed in the following proportions to prepare the mother liquid crystal composition B.

|  | wt. % |
| --- | --- |
| $R^{11} = C_3H_7$ | 24.0 |
| $R^{11} = C_5H_{11}$ | 36.0 |
| $R^{11} = C_7H_{15}$ | 25.0 |
| $R^{12} = C_5H_{11}$ | 15.0 |
|  | 100.0 |

Δn=0.137

EXAMPLE 1

Synthesis of 2-(4-propylphenyl)-5-(2,3-difluoro-4-propyloxyphenyl)-6,6-difluoro-tetrahydropyran (9)

Step 1: Synthesis of 4-(1-oxo-3-chloropropyl) propylbenzene (2)

A mixture of 120.0 g (1.0 mol) of propylbenzene (1), 139.7 g (1.1 mol) of 3-chloropropionly chloride, 146.7 g (1.1 mol) of aluminum chloride, and 1,200 ml of methylene chloride was stirred for 12 hours while being heated and refluxed in a nitrogen atmosphere. After completion of the reaction, the mixed solution was cooled to room temperature, and added dropwise into 1,500 ml of 1N diluted hydrochloric acid while being cooled. After the completion of dropping, solids were removed by filtration, the organic layer extracted by toluene from the filtrate was washed once by 1,500 ml of water, and dried over anhydrous magnesium sulfate. The solvent was distilled off under reduced pressure, and the residue was purified by silica-gel column chromatography (eluent: hexane) to obtain 4-(1-oxo-3-chloropropyl)propylbenzene (2)(84.2 g, 0.40 mol; yield: 40%). MS/211($M^+$)

Step 2: Synthesis of diethyl-2-(2,3-difluoro-4-propyloxyphenyl)malonate

To a solution prepared by dissolving 258.0 g (1.0 mol) of ethyl 2,3-difluoro-4-propyloxyphenylacetate (3) in 800 ml of diethyl ether, a solution of 107 g (1.0 mol) of lithium diisopropylamide in 500 ml of tetrahydrofuran was added dropwise at −78° C. over 30 minutes, and the resultant solution was then stirred for 1 hour. At the same temperature, a solution of 108.5 g (1.0 mol) of ethyl chloroformate in 300 ml of diethyl ether was added dropwise into the reaction solution over 30 minutes, then the temperature was raised gradually to 0° C. and stirring was continued for 12 hours. After completion of the reaction, 1,000 ml of water was added to the solution, and extraction was performed through use of 1,000 ml of hexane. The extracted organic layer was washed once with 800 ml of water, and dried over anhydrous magnesium sulfate. The solvent was distilled off under reduced pressure, and the residue was purified by silica-gel column chromatography (eluent: hexane) to obtain diethyl 2-(2,3-difluoro-4-propyloxyphenyl) malonate (4) (217.8 g, 0.66 mol; yield: 66%). MS/330($M^+$)

Step 3: Synthesis of diethyl 2-(2,3-difluoro-4-propyloxyphenyl)-2-(3-oxo-3-(4-propylphenyl) propyl) malonate (5)

To a solution of 132.0 g (0.40 mol) of diethyl 2-(2,3-difluoro-4-propyloxyphenyl) malonate (4) obtained in Step 2 in 500 ml of diethyl ether, a solution of 40.8 g (0.60mol) of sodium ethoxide in 300 ml of diethyl ether was added dropwise at −10° C. over 30 minutes, and the resultant solution was stirred for 2 hours. Subsequently, a solution of 84.2 g (0.40 mol) of 4-(1-oxo-3-chloropropyl) propylbenzene (2) synthesized in Step 1 in 200 ml of diethyl ether was added dropwise over 30 minutes, and the resultant solution was stirred for 8 hours at room temperature to allow reaction. After completion of the reaction, 400 ml of water was added, and extraction was performed through use of 4000 ml of toluene. The extracted organic layer was dried over anhydrous magnesium sulfate. The solvent was distilled off under reduced pressure, and the residue was purified by silica-gel column chromatography (eluent: hexane) to obtain diethyl 2-(2,3-difluoro-4-propyloxyphenyl)-2-(3-oxo-3-(4-propylphenyl)propyl)malonate (5)(85.7 g, 0.17 mol; yield: 43%). MS/505($M^+$)

Step 4: Synthesis of 2-(2,3-difluoro-4-propyloxyphenyl)-5-(4-propylphenyl)-5-oxopentanoate (6)

To a solution of 0.20 mol of sodium hydroxide in 200 ml of water/ethanol (1/1) mixed solvent, 85.7 g (o.17 mol) of diethyl 2-(2,3-difluoro-4-propyloxyphenyl)-2-(3-oxo-3-(4-propylphenyl)propyl)malonate (5) obtained in Step 3 was added dropwise while being cooled with ice. After the reaction solution was heated and refluxed for 5 hours, the solution was cooled to room temperature, 1N-HCl was added to adjust pH to about 2, and the solution was heated and refluxed again. After the completion of reaction, the reaction solution was condensed under reduced pressure until its volume became almost half, and extraction was performed with ethyl acetate. The extracted organic layer was dried over anhydrous magnesium sulfate. The solvent was distilled off under reduced pressure, and the residue was purified by recrystallization (solvent: acetic acid) to obtain 2-(2,3-difluoro-4-propyloxyphenyl)-5-(4-propylphenyl)-5-oxopentanoate (6) (38.0 g, 0.094 mol; yield: 55%). MS/404 ($M^+$)

Step 5: Synthesis of 4-(2-oxa-3-oxo-4-(2,3-difluoro-4-propyloxyphenyl)cyclohexyl)propylbenzene (7)

A solution of 38.0 g (0.094 mol) of 2-(2,3-difluoro-4-propyloxyphenyl)-5-(4-propylphenyl)-5-oxopentanoate (6) obtained in Step 4 in 200 ml of ethanol was cooled to −10° C., and 1.33 g (0.035 mol) of SBH was added. The reaction solution was gradually heated to room temperature, and allowed to react for 8 hours. After the completion of reaction, 100 ml of water was added under cooling with ice, and 0.1N diluted hydrochloric acid was added to adjust pH to about 4. The reaction solution was heated and allowed to react for one hour at 70° C. After the completion of reaction, the reaction solution was condensed under reduced pressure until its volume became almost half, and extraction was performed with ethyl acetate. The extracted organic layer was dried over anhydrous magnesium sulfate. The solvent was distilled off under reduced pressure, and the residue was purified by silica gel column chromatography (eluent: toluene) to obtain 4-(2-oxa-3-oxo-4-(2,3-difluoro-4-propyloxyphenyl)cyclohexyl)propylbenzene (7)(28.3 g, 0.073 mol; yield: 78%). MS/388 ($M^+$)

41

Step 6: Synthesis of 4-(2-oxa-3-thio-4-(2,3-difluoro-4-propyloxyphenyl)cyclohexyl)propylbenzene (8)

A mixture of 28.3 g (0.073 mol) of 4-(2-oxa-3-oxo-4-(2,3-difluoro-4-propyloxyphenyl)cyclohexyl)propylbenzene (7) obtained in Step 5, 44.5 g (0.11 mol) of Lawesson's reagent, and 200 ml of toluene was allowed to react in a sealed tube at 140° C. for 3 hours. The reaction mixture was added to 300 ml of water, and extraction was performed with 200 ml of toluene. The extracted organic layer was washed once with 200 ml of water, and dried over anhydrous magnesium sulfate. The solvent was distilled off under reduced pressure, and the residue was purified by silica gel column chromatography (eluent: hexane) to obtain 4-(2-oxa-3-thio-4-(2,3-difluoro-4-propyloxyphenyl)cyclohexyl) propylbenzene (8)(14.5 g, 0.036 mol; yield: 49%). MS/405 (M$^+$)

Step 7: Synthesis of 2-(4-propylphenyl)-5-(2,3-difluoro-4-propyloxyphenyl)-6,6-difluoro-tetrahydropyran (9)

To a solution of 14.5 g (0.036 mol) of 4-(2-oxa-3-thio-4-(2,3-difluoro-4-propyloxyphenyl)cyclohexyl) propylbenzene (8) obtained in Step 6 in 60 ml of methylene chloride, a solution of 8.7 g (0.54 mol) of DAST in 40 ml of methylene chloride was added dropwise at 0° C. over 30 minutes. After completion of addition, the mixed solution was heated to room temperature, and allowed to react for 12 hours. After the completion of reaction, 100 ml of water was added to the reaction solution, and was extraction was performed with 200 ml of toluene. The extracted organic layer was washed once with 100 ml of water, and dried over anhydrous magnesium sulfate. The solvent was distilled off under reduced pressure, and the residue was purified by silica gel column chromatography (eluent: hexane/toluene=1/1), and further by recrystallization from hexane to obtain 2-(4-propylphenyl)-5-(2,3-difluoro-4-propyloxyphenyl)-6,6-difluoro-tetrahydropyran (9) (5.7 g, 0.014 mol; yield: 38%). MS/410 (M$^+$), Δε=−6.8, Δn=0.139

EXAMPLE 2

Synthesis of 2-(4-(4-pentylcyclohexyl) cyclohexyl)-5-iodo-6,6-difluorotetrahydropyran (16)

Step 1: Synthesis of 4-hydroxy-4-(4-(4-pentylcyclohexyl) cyclohexyl)butanal propylene acetal (11)

To Grignard reagent prepared from 33.7 g (173 mmol) of 2-(2-bromoethyl)-1,3-dioxane and magnesium in 300 ml of tetrahydrofuran (THF), a solution of 40.0 g (151 mmol) of 4-(4-pentylcyclohexyl) cyclohexane carbaldehyde (10) in 200 ml of THF was added dropwise, and the resultant solution was stirred for 3 hours. The reaction solution was added into 500 ml of 1N-hydrochloric acid, and the reaction product was extracted with 300 ml of toluene. The formed organic layer was sequentially washed with a saturated aqueous solution of hydrogen sodium carbonate and water, and dried over anhydrous magnesium sulfate. The solvent was distilled off under reduced pressure, and the residue was purified by silica gel column chromatography (eluent: hexane) to obtain 47.5 g (125 mmol) of 4-hydroxy-4-(4-(4-pentylcyclohexyl) cyclohexyl)butanal propylene acetal (11) at a yield of 82.8 percent.

Step 2: Synthesis of 1,3-dioxane-2-ylethyl 4-(4-pentylcyclohexyl) cyclohexyl ketone (12)

A solution of 25.0 g (197 mmol) of oxalyl chloride in 1000 ml of methylene chloride was cooled to −65° C. in a nitrogen atmosphere, and while this temperature was maintained, a solution of 20.8 g (263 mmol) of dimethyl sulfoxide in 100 ml of methylene chloride was added dropwise. After the solution was stirred for 10 minutes, a solution of 38.0 g (100 mmol) of 4-hydroxy-4-(4-(4-pentylcyclohexyl) cyclohexyl)butanal propylene acetal (11) obtained in Step 1 in 500 ml of methylene chloride was added dropwise. After this solution was stirred at −65° C. for 15 minutes, then at −45° C. for 1 hour, 74.0 g (731 mmol) of triethylamine was added dropwise. After the reaction solution was heated to 0° C. and stirred for 20 minutes, 300 ml of a saturated aqueous solution of ammonium chloride, 500 ml of water, and 500 ml of methylene chloride were added. The organic layer was separated, washed sequentially with 0.5N-hydrochloric acid, a saturated aqueous solution of hydrogen sodium carbonate, and water, and dried over anhydrous magnesium sulfate. The solvent was distilled off under reduced pressure, and the residue was purified by silica gel column chromatography (eluent: heptane/ethyl acetate=3/1) to obtain 26.3 g (69.5 mmol) of 1,3-dioxane-2-ylethyl 4-(4-pentylcyclohexyl) cyclohexyl ketone (12) at a yield of 69.5 percent.

Step 3: Synthesis of 4-oxo-4-(4-pentylcyclohexyl) cyclohexylbutanal (13)

To 26.3 g (69.5 mmol) of 1,3-dioxane-2-ylethyl 4-(4-pentylcyclohexyl) cyclohexyl ketone (12) obtained in Step 2, 300 ml of formic acid was added and the resultant solution was heated and refluxed for 3 hours. After 500 ml of water was added to the reaction solution, the product was extracted with 500 ml of toluene. The organic layer was washed sequentially with water, a saturated aqueous solution of hydrogen sodium carbonate, and water, and dried over anhydrous magnesium sulfate. The solvent was distilled off under reduced pressure to obtain 180 g (56.2 mmol) of 4-oxo-4-(4-pentylcyclohexyl) cyclohexylbutanal (13) at a yield of 80.4 percent.

Step 4: Synthesis of 4,4-difluoro-3-butenyl 4-(4-pentylcyclohexyl) cyclohexyl ketone (14)

In 150 ml of N,N-dimethylformamide, 180 g (56.2 mmol) of 4-oxo-4-(4-pentylcyclohexyl) cyclohexylbutanal (13) obtained in Step 3 and 22.0 g (83.7 mmol) of triphenyl phosphine were dissolved and heated to 100° C. To this solution, 18.3 g (120 mmol) of sodium chlorodifluoroacetate was added slowly, and the solution was stirred for 1 hour and cooled to room temperature. The reaction solution was filtered by use of celite, and the solvent was distilled off from the filtrate under reduced pressure. To the residue, 500 ml of water and 500 ml of toluene were added to extract the reaction product. The organic layer was dried over anhydrous magnesium sulfate, and the solvent was distilled off under reduced pressure. The residue was purified by silica-gel column chromatography (eluent: toluene) to obtain 7.0 g (20 mmol) of 4,4-difluoro-3-butenyl 4-(4-pentylcyclohexyl) cyclohexyl ketone (14) at a yield of 36 percent.

Step 5: Synthesis of 1-(4-(4-pentylcyclohexyl) cyclohexyl)-4,4-difluoro-3-butene-1-ol(15)

In a mixed solvent of ethanol/THF (=10/1), 7.0 g (20 mmol) of 4,4-difluoro-3-butenyl 4-(4-pentylcyclohexyl) cyclohexyl ketone (14) obtained in Step 4 was dissolved, and the solution was cooled to 10° C. To this solution, 0.34 g (9.0 mmol) of SBH was added slowly, and the solution was stirred for 2 hours while this temperature was maintained. After 50 ml of 2N-hydrochloric acid was added to the reaction solution, the reaction product was extracted with toluene. The organic layer was washed sequentially with a saturated aqueous solution of hydrogen sodium carbonate and water, and dried over anhydrous magnesium sulfate. The solvent was distilled off under reduced pressure, and the residue was purified by silica-gel column chromatography (eluent: toluene) to obtain 4.7 g (13 mmol) of 1-(4-(4- pentylcyclohexyl) cyclohexyl)-4,4-difluoro-3-butene-1-ol (15) at a yield of 65 percent.

Step 6: Synthesis of 2-(4-(4-pentylcyclohexyl) cyclohexyl)-5-iodo-6,6-difluorotetrahydropyran (16)

To 35 ml of acetonitrile, 8.2 g of iodine was added, and 3.8 g (11 mmol) of 1-(4-(4-pentylcyclohexyl) cyclohexyl)-4,4-difluoro-3-butene-1-ol(15) obtained in Step 5 suspended in 200 ml of acetonitrile was added dropwise to the mixture, and the mixture was stirred for 3 hours at room temperature. To the reaction solution, 100 ml of sodium thiosulfate was added, and the reaction product was extracted with toluene. The organic layer was washed with water, and dried over anhydrous magnesium sulfate. The solvent was distilled off under reduced pressure, and the residue was purified by silica-gel column chromatography (eluent: heptane/toluene= 1/1) and recrystallized from 2 ml of heptane to obtain 1.0 g (2.1 mmol) of 2-(4-(4-pentylcyclohexyl) cyclohexyl) -5-iodo-6, 6-difluorotetrahydropyran (16) at a yield of 19 percent.

The properties of the product are as follows: Phase transition temperature: Sx-N 141.4° C., N-I 160.7° C.; 1H-NMR(CDCl3) δ(ppm): 4.07–3.99 (m, 1H), 3.82–3.78 (m, 1H)), 2.45–2.42 (m, 1H), 2.35–2.30 (m, 1H), 1.97–0.81 (m, 33H) Δε=–2.52, Δn=0.132

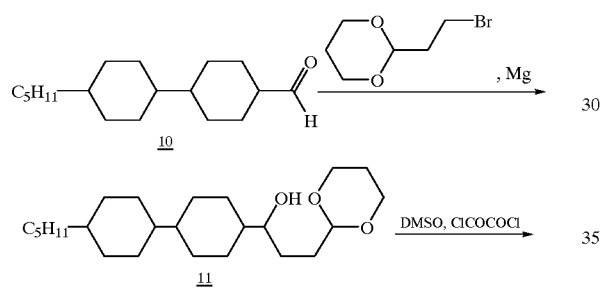

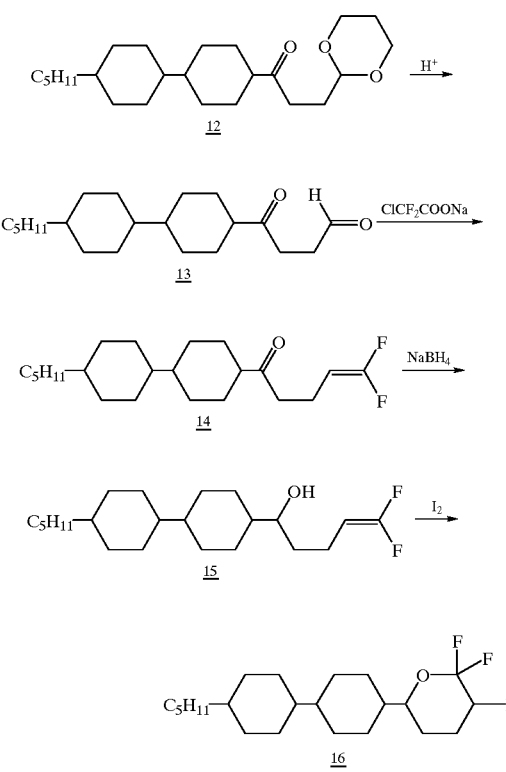

According to the methods of Examples 1 and 2, the following compounds can be synthesized.

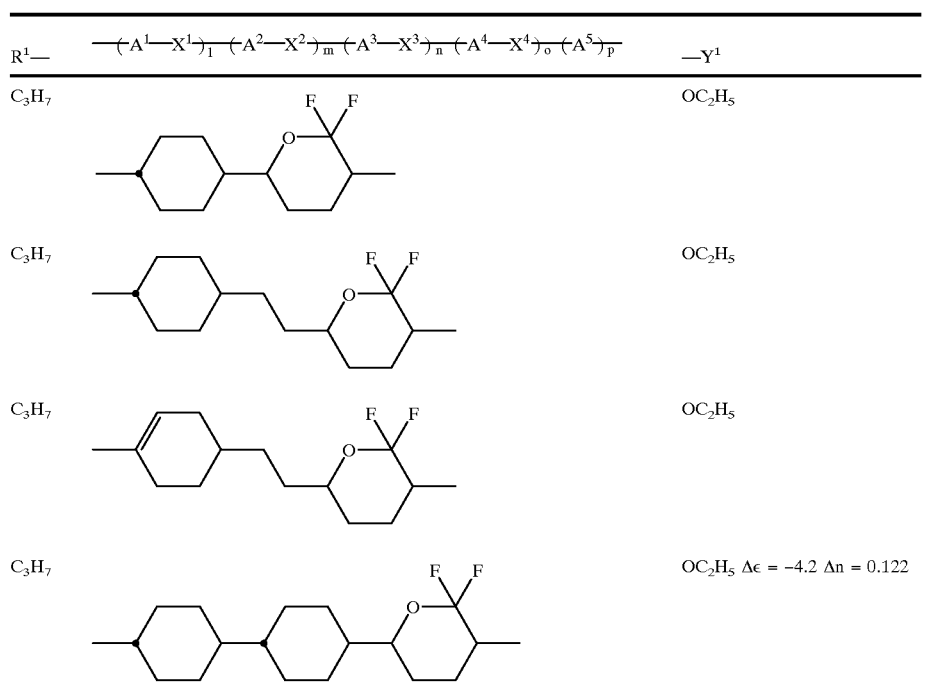

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | 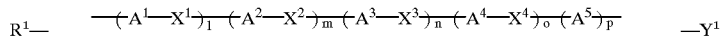 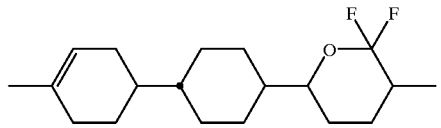 | OC₂H₅ |
| C₃H₇ | 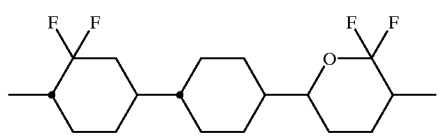 | OC₂H₅ |
| C₃H₇ | 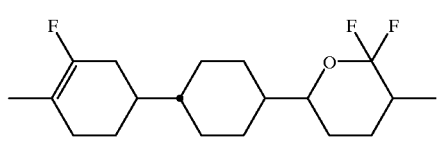 | OC₂H₅ |
| C₃H₇ | 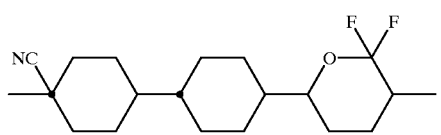 | OC₂H₅ |
| C₃H₇ | 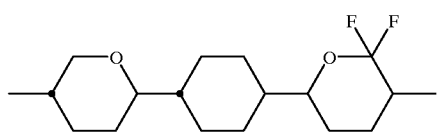 | OC₂H₅ |
| C₃H₇ | 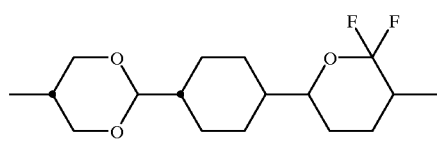 | OC₂H₅ |
| C₃H₇ | 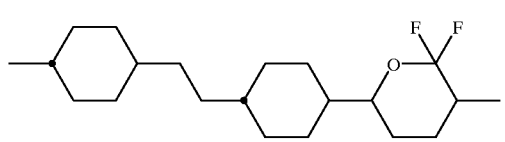 | OC₂H₅ |
| C₃H₇ | 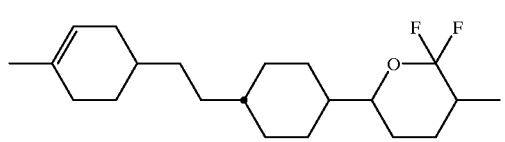 | OC₂H₅ |
| C₃H₇ | 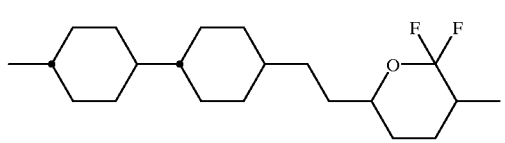 | OC₂H₅ |
| C₃H₇ | 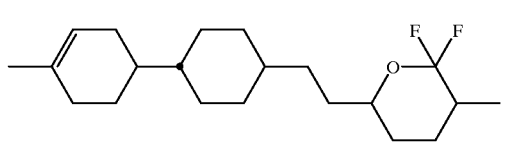 | OC₂H₅ |

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | C₃H₇ |
| C₃H₇ | | C₃H₇ |
| C₃H₇ | | C₃H₇ |
| C₃H₇ | | C₃H₇ Δε = −2.4 Δn = 0.122 |
| C₃H₇ | | C₃H₇ |
| C₃H₇ | | C₃H₇ |
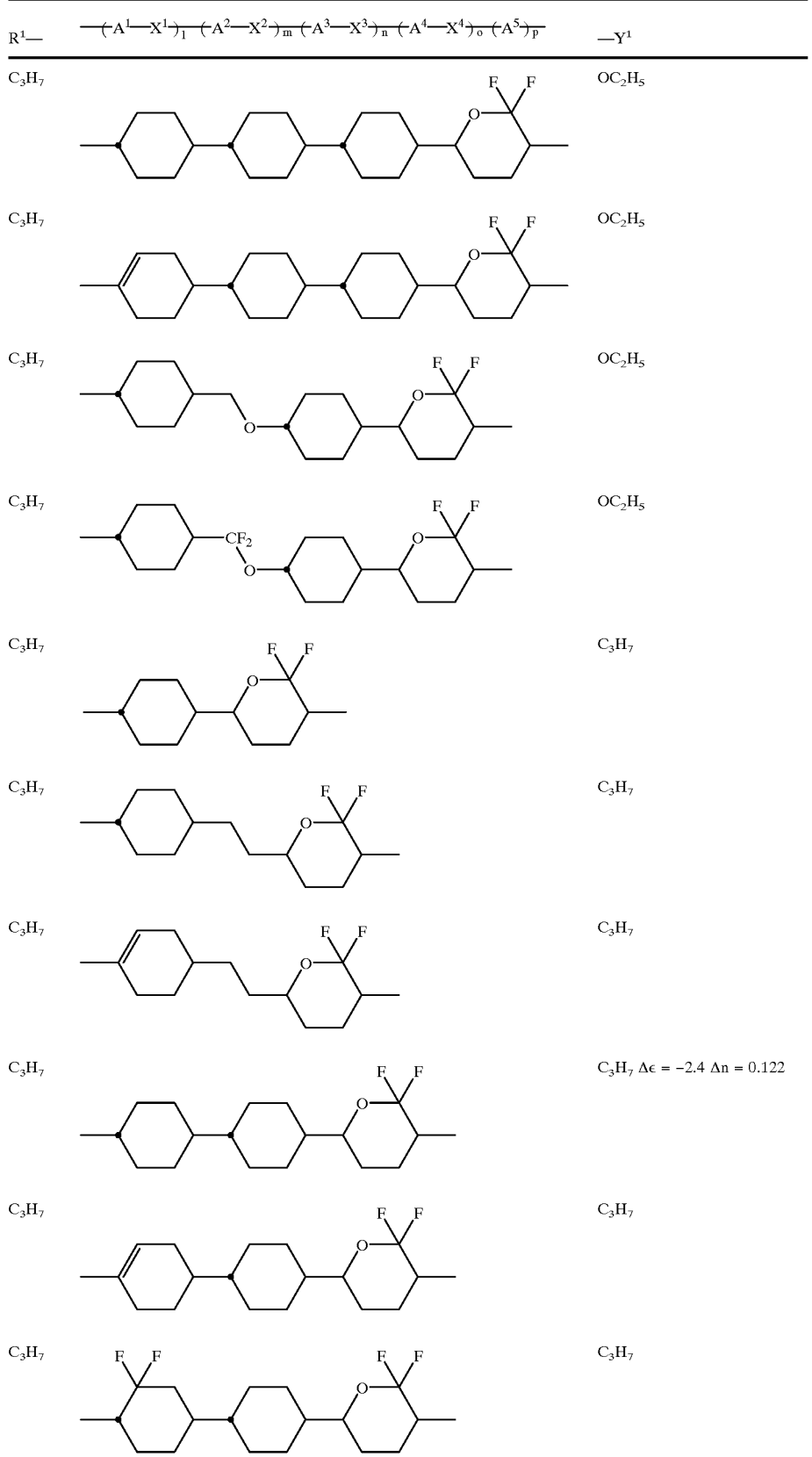

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | 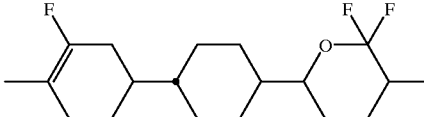 | C₃H₇ |
| C₃H₇ | 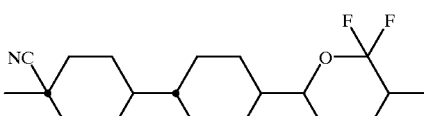 | C₃H₇ |
| C₃H₇ | 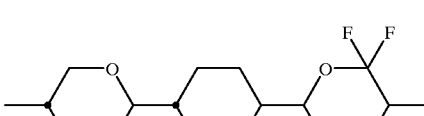 | C₃H₇ |
| C₃H₇ | 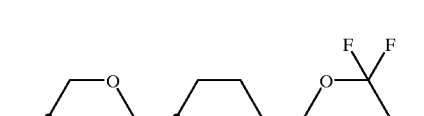 | C₃H₇ |
| C₃H₇ | 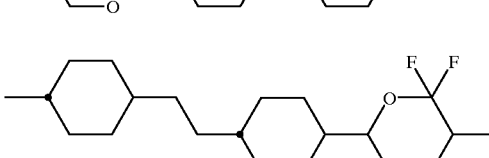 | C₃H₇ |
| C₃H₇ | 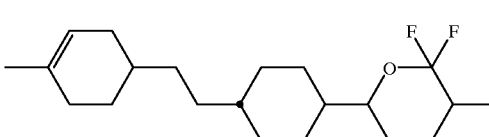 | C₃H₇ |
| C₃H₇ | 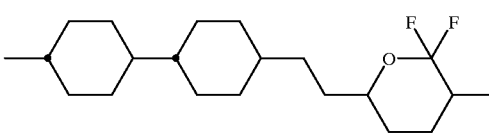 | C₃H₇ |
| C₃H₇ | 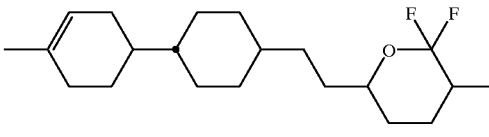 | C₃H₇ |
| C₃H₇ | 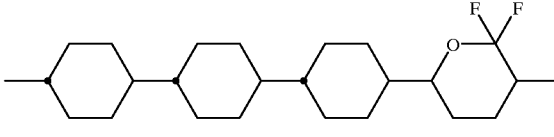 | C₃H₇ |
| C₃H₇ | 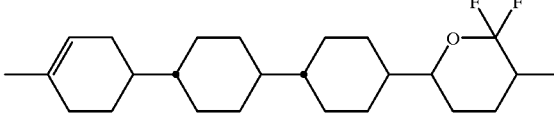 | C₃H₇ |

-continued

| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | | C₃H₇ |
| C₃H₇ | | C₃H₇ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |

-continued

| R¹— | —(A¹—X¹)ₗ—(A²—X²)ₘ—(A³—X³)ₙ—(A⁴—X⁴)ₒ—(A⁵)ₚ— | —Y¹ |
|---|---|---|
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | OC₂H₅ |
| C₃H₇ | | C₃H₇ |

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
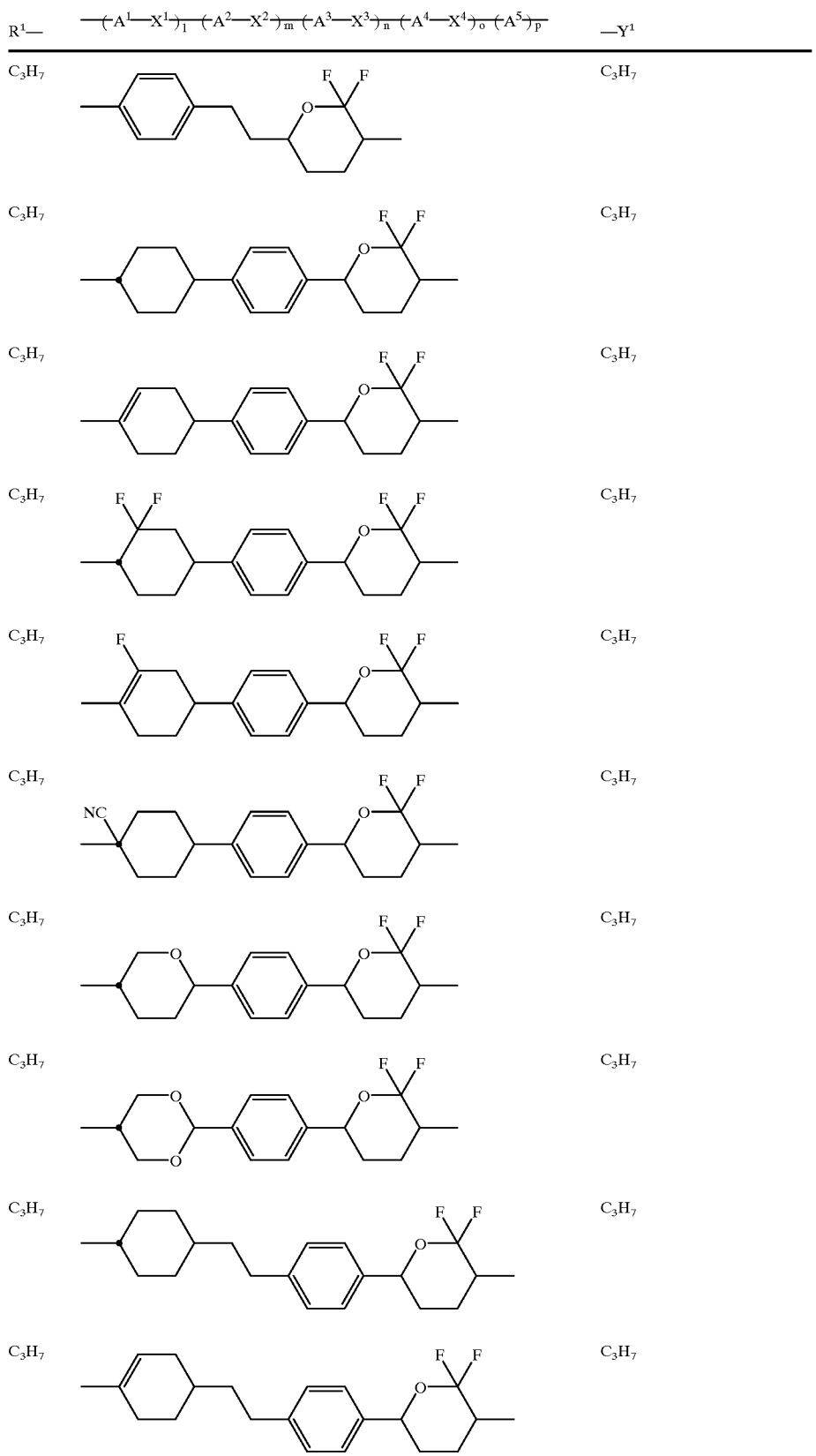

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | 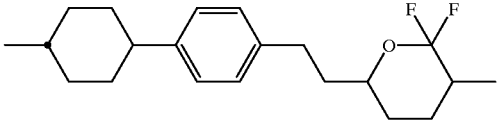 | C₃H₇ |
| C₃H₇ | 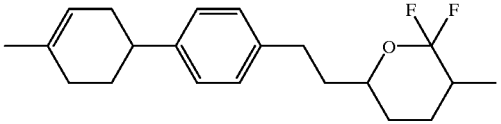 | C₃H₇ |
| C₃H₇ | 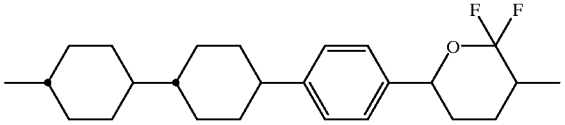 | C₃H₇ |
| C₃H₇ | 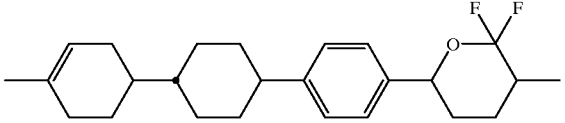 | C₃H₇ |
| C₃H₇ | 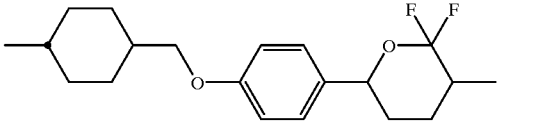 | C₃H₇ |
| C₃H₇ | 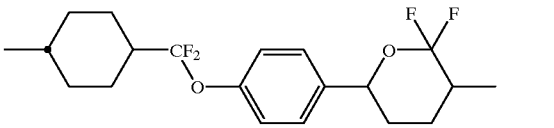 | C₃H₇ |
| C₃H₇ | 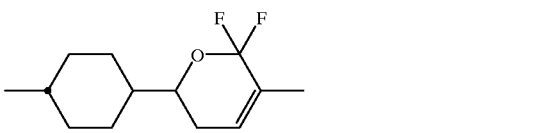 | C₃H₇ |
| C₃H₇ | 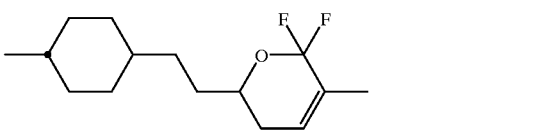 | C₃H₇ |
| C₃H₇ |  | C₃H₇ |
| C₃H₇ | 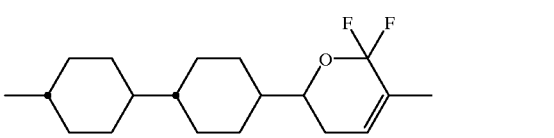 | C₃H₇ |

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | 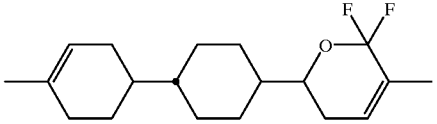 | C₃H₇ |
| C₃H₇ | 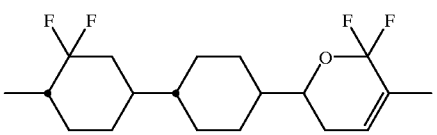 | C₃H₇ |
| C₃H₇ | 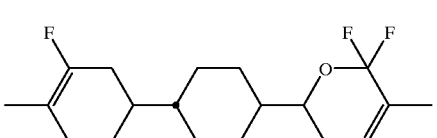 | C₃H₇ |
| C₃H₇ | 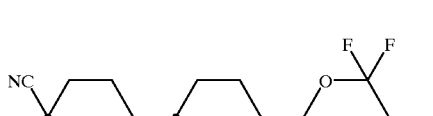 | C₃H₇ |
| C₃H₇ | 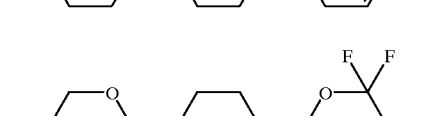 | C₃H₇ |
| C₃H₇ | 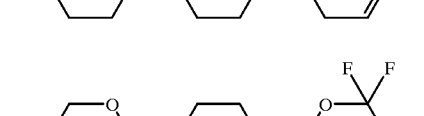 | C₃H₇ |
| C₃H₇ | 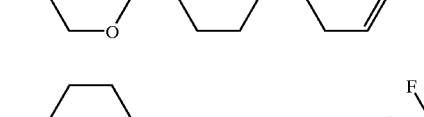 | C₃H₇ |
| C₃H₇ | 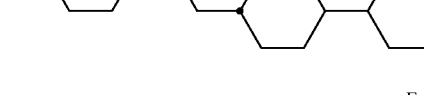 | C₃H₇ |
| C₃H₇ | 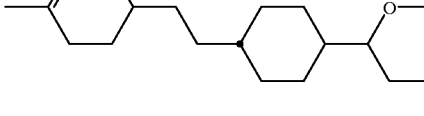 | C₃H₇ |
| C₃H₇ | 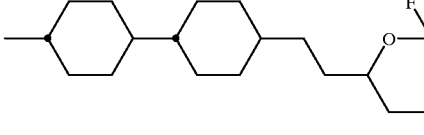 | C₃H₇ |

-continued
| $R^1$— | $-(A^1-X^1)_l-(A^2-X^2)_m-(A^3-X^3)_n-(A^4-X^4)_o-(A^5)_p$ | $-Y^1$ |
|---|---|---|
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
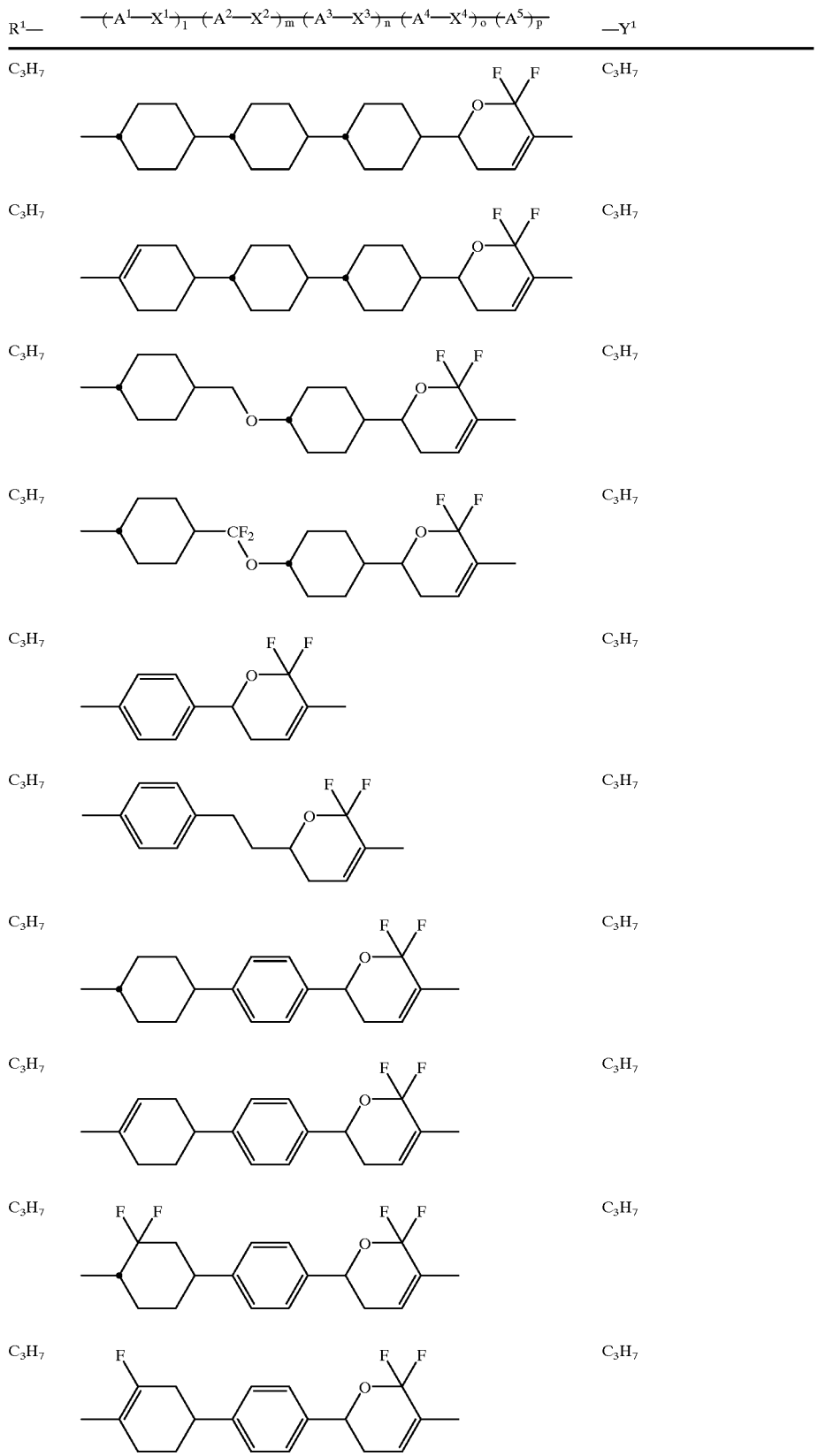

-continued
| R¹— | ─(A¹─X¹)ₗ─(A²─X²)ₘ─(A³─X³)ₙ─(A⁴─X⁴)ₒ─(A⁵)ₚ─ | —Y¹ |
|---|---|---|
| C₃H₇ | 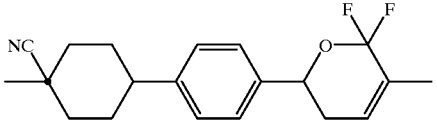 | C₃H₇ |
| C₃H₇ | 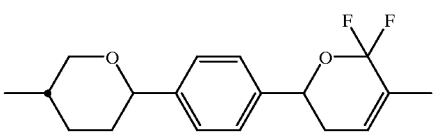 | C₃H₇ |
| C₃H₇ | 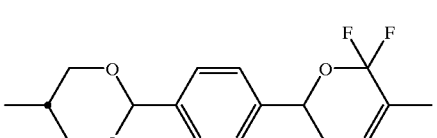 | C₃H₇ |
| C₃H₇ | 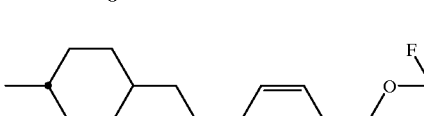 | C₃H₇ |
| C₃H₇ | 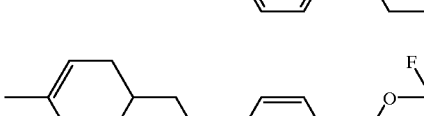 | C₃H₇ |
| C₃H₇ | 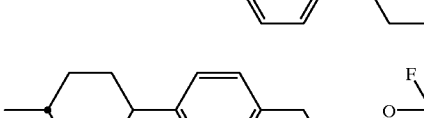 | C₃H₇ |
| C₃H₇ | 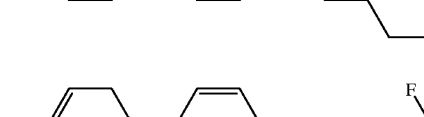 | C₃H₇ |
| C₃H₇ | 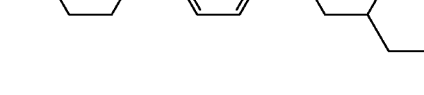 | C₃H₇ |
| C₃H₇ | 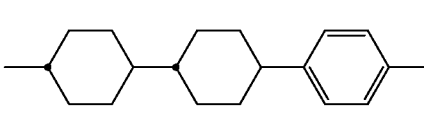 | C₃H₇ |
| C₃H₇ | 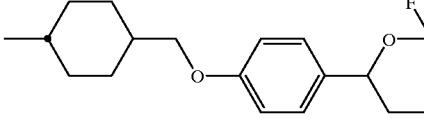 | C₃H₇ |

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | 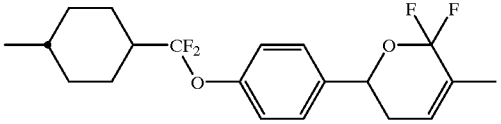 | C₃H₇ |
| C₃H₇ | 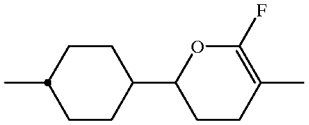 | C₃H₇ |
| C₃H₇ | 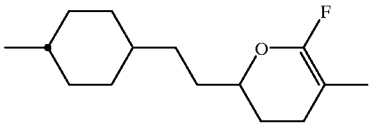 | C₃H₇ |
| C₃H₇ | 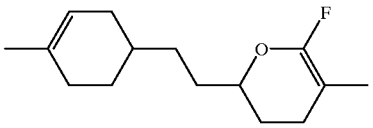 | C₃H₇ |
| C₃H₇ | 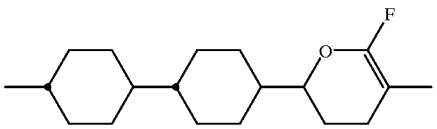 | C₃H₇ |
| C₃H₇ | 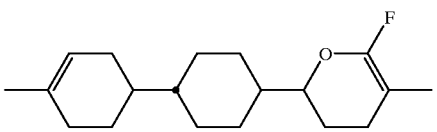 | C₃H₇ |
| C₃H₇ | 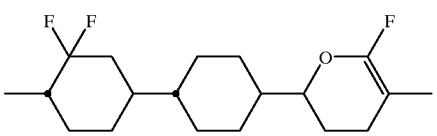 | C₃H₇ |
| C₃H₇ | 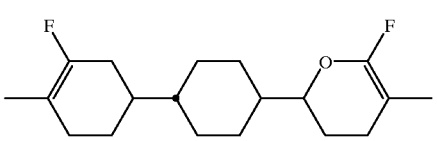 | C₃H₇ |
| C₃H₇ | 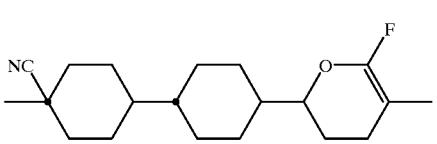 | C₃H₇ |
| C₃H₇ | 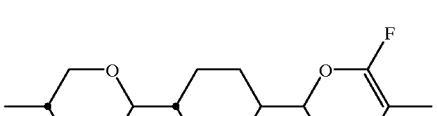 | C₃H₇ |

-continued
| R¹— | —(A¹—X¹)ₗ—(A²—X²)ₘ—(A³—X³)ₙ—(A⁴—X⁴)ₒ—(A⁵)ₚ— | —Y¹ |
|---|---|---|
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
| C₃H₇ | | C₃H₇ |
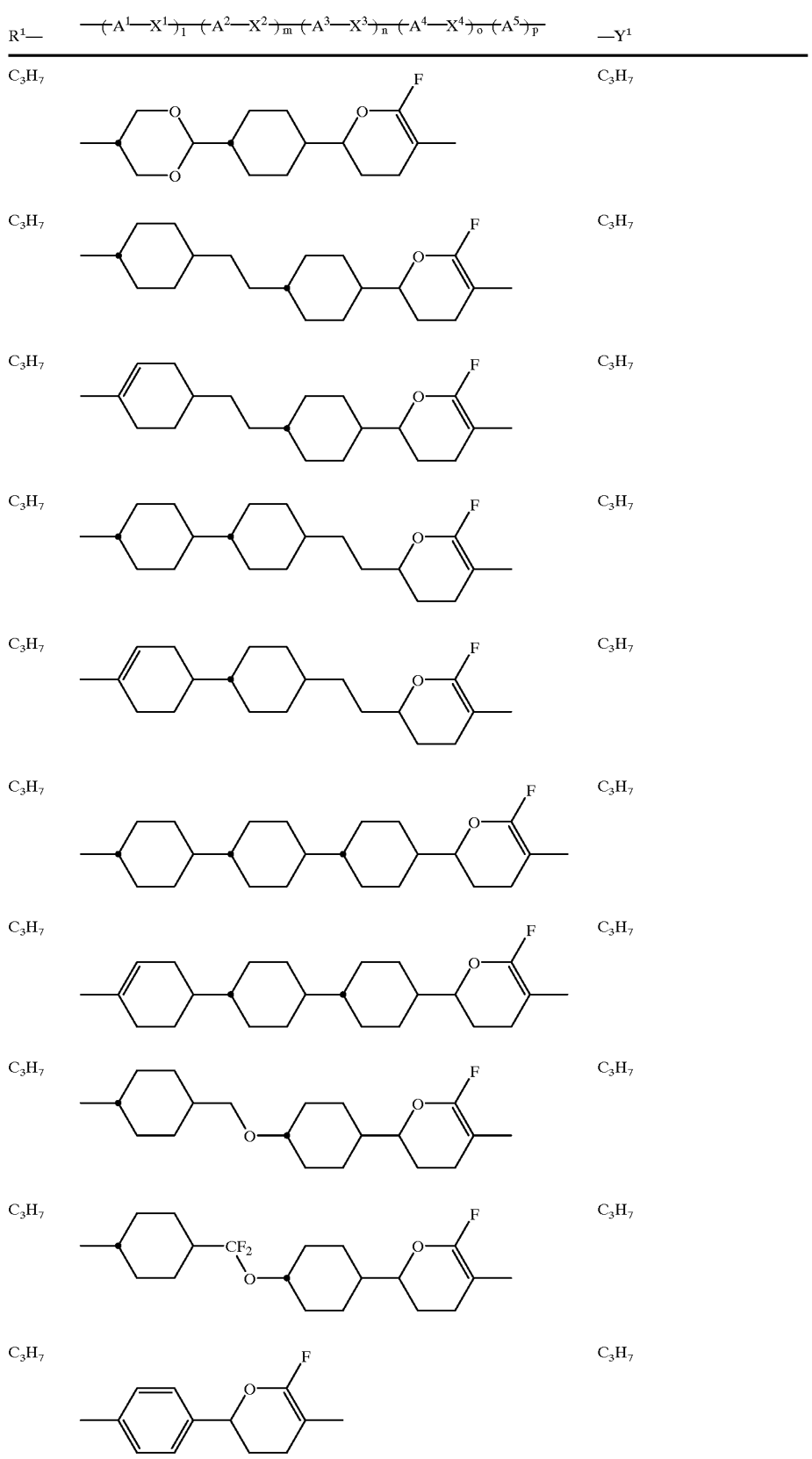

-continued
| R¹— | ―(A¹―X¹)ₗ―(A²―X²)ₘ―(A³―X³)ₙ―(A⁴―X⁴)ₒ―(A⁵)ₚ | —Y¹ |
|---|---|---|
| C₃H₇ | 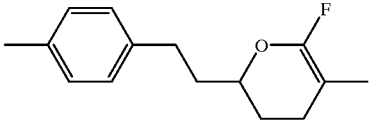 | C₃H₇ |
| C₃H₇ | 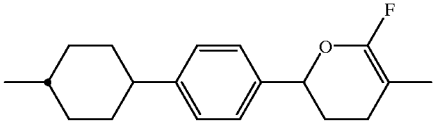 | C₃H₇ |
| C₃H₇ | 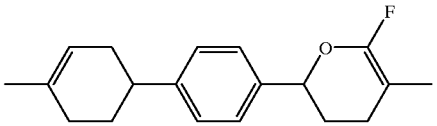 | C₃H₇ |
| C₃H₇ | 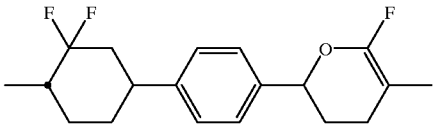 | C₃H₇ |
| C₃H₇ | 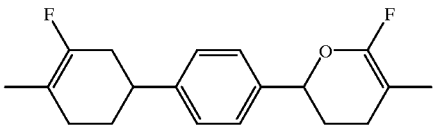 | C₃H₇ |
| C₃H₇ | 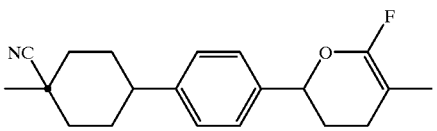 | C₃H₇ |
| C₃H₇ | 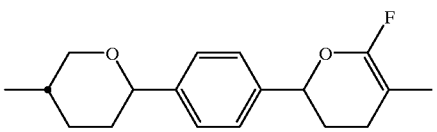 | C₃H₇ |
| C₃H₇ | 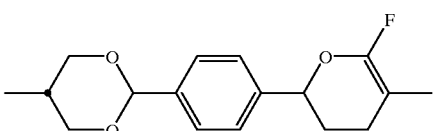 | C₃H₇ |
| C₃H₇ | 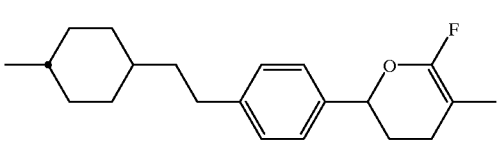 | C₃H₇ |
| C₃H₇ | 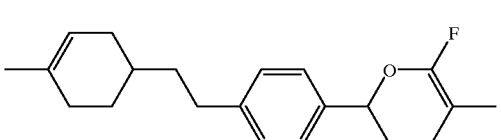 | C₃H₇ |

-continued
| $R^1-$ | $-(A^1-X^1)_l-(A^2-X^2)_m-(A^3-X^3)_n-(A^4-X^4)_o-(A^5)_p$ | $-Y^1$ |
|---|---|---|
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | $C_3H_7$ |
| $C_3H_7$ | | I |
| $C_3H_7$ | | I |
| $C_3H_7$ | | I |
| $C_5H_{11}$ | | I $\Delta\epsilon = -2.52$ $\Delta n = 0.132$ |
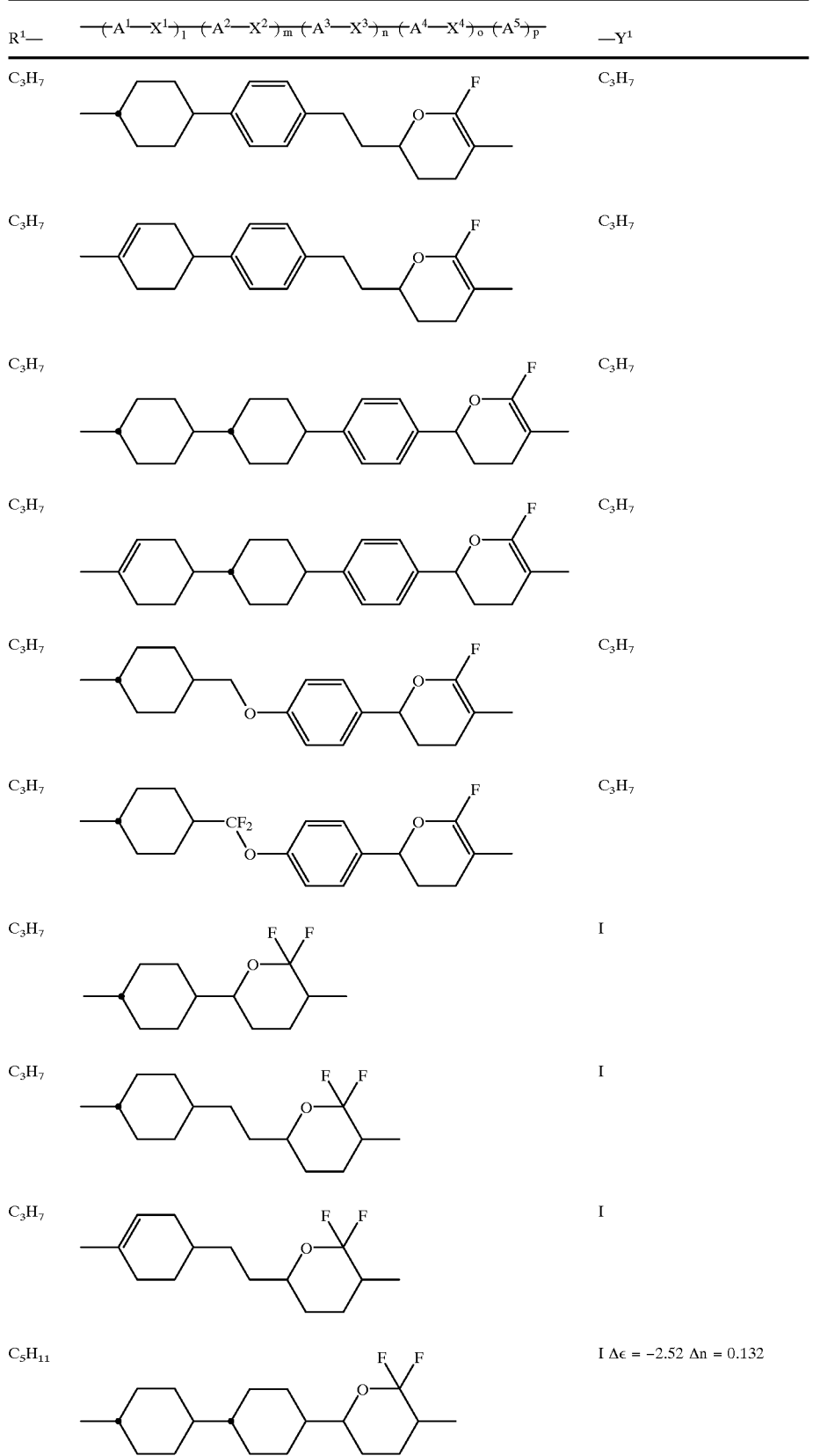

-continued
| R¹— | —(A¹—X¹)ₗ—(A²—X²)ₘ—(A³—X³)ₙ—(A⁴—X⁴)ₒ—(A⁵)ₚ | —Y¹ |
|---|---|---|
| C₃H₇ | 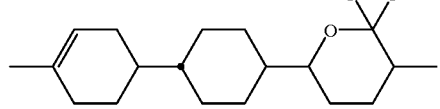 | I |
| C₃H₇ | 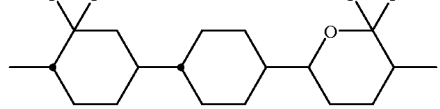 | I |
| C₃H₇ | 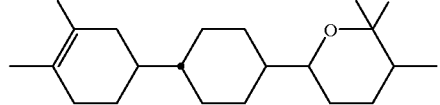 | I |
| C₃H₇ | 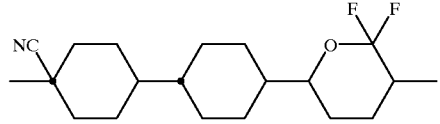 | I |
| C₃H₇ | 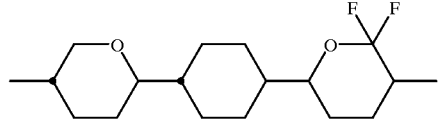 | I |
| C₃H₇ | 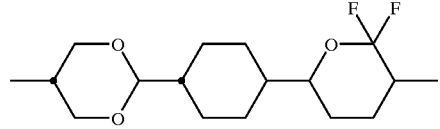 | I |
| C₃H₇ | 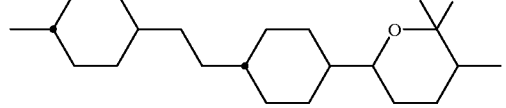 | I |
| C₃H₇ | 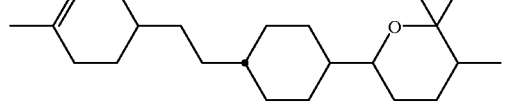 | I |
| C₃H₇ | 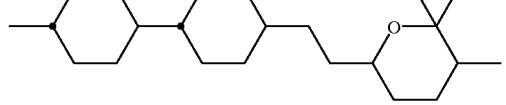 | I |
| C₃H₇ | 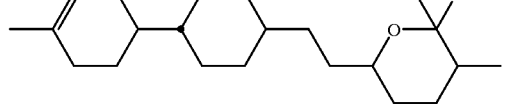 | I |

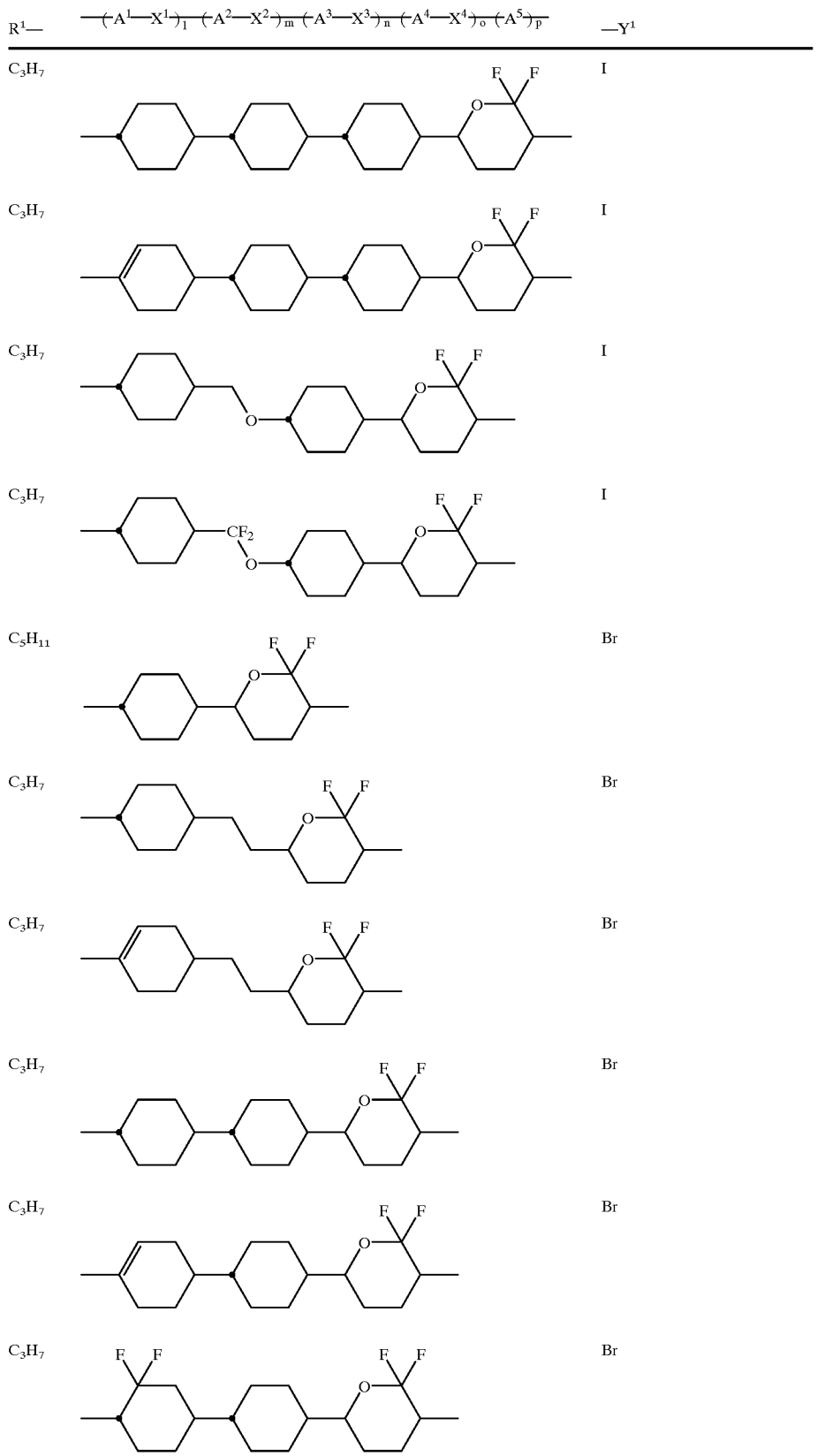

-continued
| R¹— | —(A¹—X¹)ₗ—(A²—X²)ₘ—(A³—X³)ₙ—(A⁴—X⁴)ₒ—(A⁵)ₚ— | —Y¹ |
|---|---|---|
| C₃H₇ | 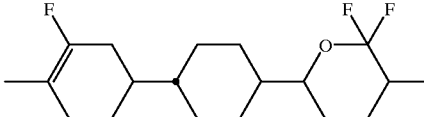 | Br |
| C₃H₇ | 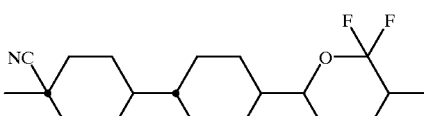 | Br |
| C₃H₇ | 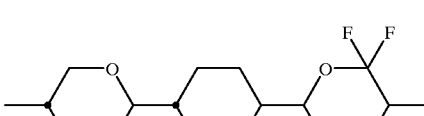 | Br |
| C₃H₇ | 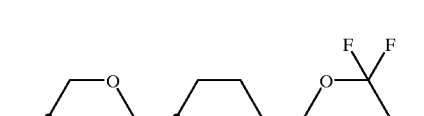 | Br |
| C₃H₇ | 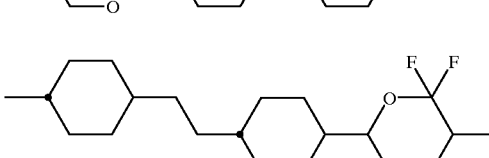 | Br |
| C₃H₇ | 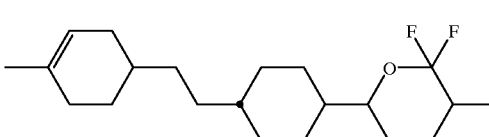 | Br |
| C₃H₇ | 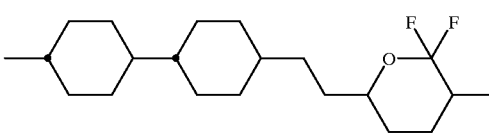 | Br |
| C₃H₇ | 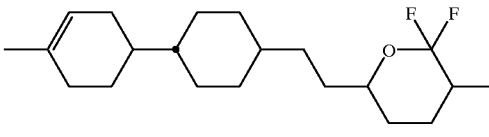 | Br |
| C₃H₇ | 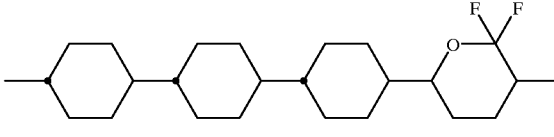 | Br |
| C₃H₇ | 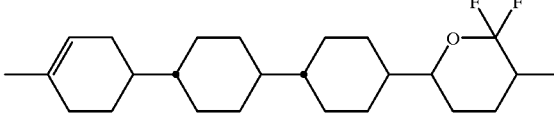 | Br |

-continued
| R¹— | $-(A^1-X^1)_l-(A^2-X^2)_m-(A^3-X^3)_n-(A^4-X^4)_o-(A^5)_p-$ | —Y¹ |
|---|---|---|
| C₃H₇ | 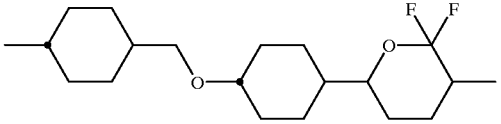 | Br |
| C₃H₇ | 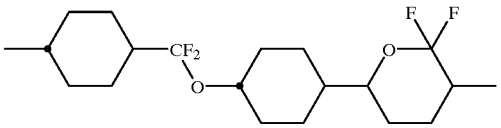 | Br |
| C₅H₁₁ | 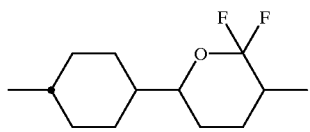 | H |
| C₃H₇ | 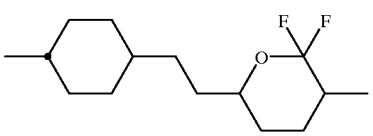 | H |
| C₃H₇ | 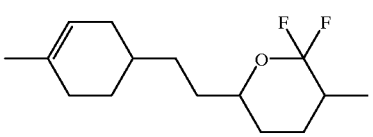 | H |
| C₃H₇ | 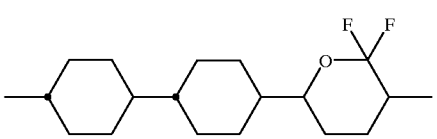 | H |
| C₃H₇ | 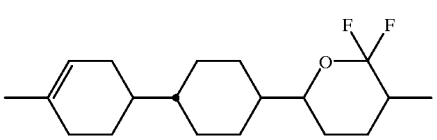 | H |
| C₃H₇ | 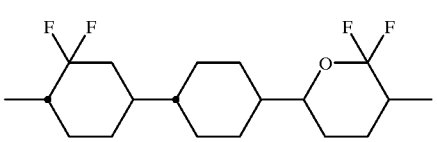 | H |
| C₃H₇ | 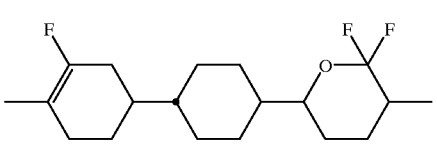 | H |
| C₃H₇ | 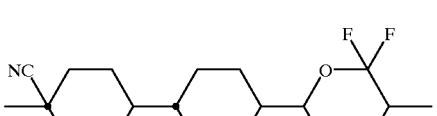 | H |

-continued

| R¹— | $-(A^1-X^1)_l-(A^2-X^2)_m-(A^3-X^3)_n-(A^4-X^4)_o-(A^5)_p-$ | —Y¹ |
|---|---|---|
| C₃H₇ | | H |
| C₃H₇ | | H |
| C₃H₇ | | H |
| C₃H₇ | | H |
| C₃H₇ | | H |
| C₃H₇ | | H |
| C₃H₇ | | H |
| C₃H₇ | | H |
| C₃H₇ | | H |
| C₃H₇ | | H |

The present invention provides a liquid crystalline compound having low viscosity, a large absolute value of negative dielectric anisotropy, controlled optical anisotropy value, high specific resistance, high voltage holding ratio, and high stability against heat and ultraviolet radiation; a liquid crystal composition prepared from such a liquid crystalline compound; and a liquid crystal display element fabricated utilizing such a liquid crystal composition.

We claim:

1. A liquid crystalline compound represented by general formula (1),

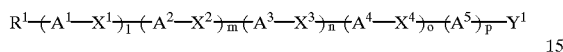

where $R^1$ and $Y^1$ independently represent an alkyl group having 1 to 20 carbon atoms, a hydrogen atom, a halogen atom, a cyano group, a cyanate group an isocyano group, or an isothiocyanate group, in which one or more nonadjacent methylene groups in said alkyl group may be substituted by an oxygen atom, a sulfur atom, a nitrogen atom, —C≡C—, a dialkylsilylene group, a monoalkylsilylene group, a silylene group, or a vinylene group, and one or more hydrogen atoms in the alkyl group may be substituted by a fluorine atom or a chlorine atom; $X^1$, $X^2$, $X^3$, and $X^4$ independently represent a single bond, —(CH$_2$)$_2$—, —C≡C—, —COO—, —OCO—, CH$_2$O—, —OCH$_2$—, —(CH$_2$)$_4$—, —(CH$_2$)$_3$O—, —O(CH$_2$)$_3$—, —CH=CHCH$_2$CH$_2$—, —CH$_2$CH=CHCH$_2$—, —CH$_2$CH$_2$CH=CH—, —CH=CHCH=CH—, —CF$_2$O—, —OCF$_2$—, —CH=CHCH$_2$O—, —OCH$_2$CH=CH—, —CF=CF—, —CH$_2$CF$_2$—, —CF$_2$CH$_2$—, —(CF$_2$)$_2$—, —(CF$_2$)$_4$—, —(CH$_2$)$_2$COO—, —OCO(CH$_2$)$_2$—, —CH=CHCOO—, —OCOCH=CH—, —CH=CHC≡C— or —C≡CCH=CH—; ring $A^1$, ring $A^2$, ring $A^3$, ring $A^4$, and ring $A^5$ independently represent trans-cyclohexane-1,4-diyl, cyclohexa-1-ene-1,4-diyl, 1,4-phenylene, bicyclo[1,1,1]pentane-1,3-diyl, 6,6-difluorotetrahydropyran-1,5-diyl, 6,6-difluoro-2,3-dihydro-6H-pyran-2,5-diyl, or 6-fluroro-3,4-diydro-2H-pyran-2,5-diyl, wherein carbon atoms constituting the ring of trans-cyclohexane-1,4-diyl, cyclohexa-1-ene-1,4-diyl or 1,4-phenylene may be substituted by nitrogen atoms, oxygen atoms, or sulfur atoms, and hydrogen atoms on the ring may be substituted by halogen atoms or cyano groups, but at least one of said rings $A^1$, $A^2$, $A^3$, $A^4$, and $A^5$ is 6,6-difluorotetrahydropyran-2,5-diyl, 6,6-difluoro-2,3-dihydro-6H-pyran-2,5-diyl, or 6-fluroro-3,4-dihydro-2H-pyran-2,5-diyl and a heterocyclic ring is not directly connected to bicyclo[1,1,1]pentane-1,3-diyl, 6,6-difluorotetrahydropyran- 2,5-kiyl, 6,6-difluoro-2,3-diyhro-6H-pyran-2,5-diyl or 6-fluoro-3,4-dihydro-2H-pyra-2,5-diyl; l, m, n, o, and p are independently 0 or 1, but 4≧l+m+n+o+p≧2; and any atom of this compound may be substituted by an isotope thereof.

2. A liquid crystal composition comprising at least one of the liquid crystalline compounds according to claim 1.

3. A liquid crystal composition containing as the first component thereof at least one of the licuid crystalline compounds according to claim 1, and as the second component thereof at least one of the compounds selected from the group consisting of compounds represented by general formulas (2), (3), or (4),

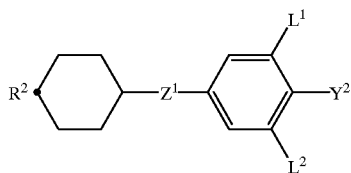

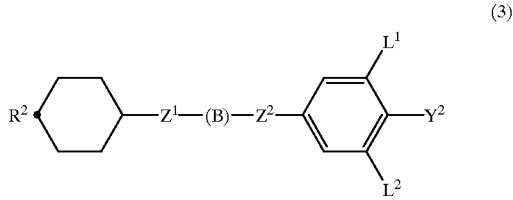

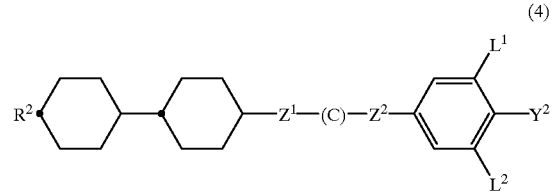

where, $R^2$ represents an alkyl group having 1 to 10 carbon atoms, in which one or more nonadjacent methylene groups in said alkyl group may be substituted by an oxygen atom or —C≡C—, and one or more hydrogen atoms in the alkyl group may be substituted by a fluorine atom; $Y^2$ represents a fluorine atom, a chlorine atom, —OCF$_3$, —CF$_2$H, —CF$_3$, —CF$_2$H, —CFH$_2$, —OCF$_2$CF$_2$H, or —OCF$_2$CFHCF$_3$; $L^1$ and $L^2$ independently represent a hydrogen atom or a fluorine atom; $Z^1$ and $Z^2$ independently represent —(CH$_2$)$_2$—, —(CH$_2$)$_4$—, —COO—, —CF$_2$O—, —OCF$_2$—, —CH=CH—, or a single bond; ring B represents trans-cyclohexane-1,4-diyl, 1,3-dioxane-2,5-diyl, or 1,4-phenylene whose hydrogen atoms may be substituted by fluorine atoms; ring C represents trans-cyclohexane-1,4-diyl, or 1,4-phenylene whose hydrogen atoms may be substituted by fluorine atoms; and any atom of this compound may be substituted by an isotope thereof.

4. A liquid crystal composition containing as the first component thereof at least one of the compounds according to claim 1, and as the second component thereof at least one of the compounds selected from the group consisting of compounds represented by general formulas (5) or (6),

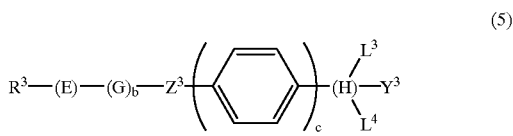

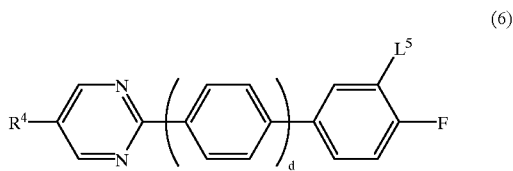

where, $R^3$ and $R^4$ independently represent an alkyl group having 1 to 10 carbon atoms, in which one or more nonadjacent methylene groups in said alkyl group may be substituted by an oxygen atom or —C≡C—, and one or more hydrogen atoms in the alkyl group may be substituted by a fluorine atom; $Y^3$ is a cyano group or —C≡C—CN; ring E represents trans-cyclohexane-1,4-diyl, 1,4-phenylene, 1,3-dioxane-2,5-diyl, or pyrimidine-2,5-diyl; ring G represents trans-cyclohexane-1,4-diyl, pyrimidine-2,5-diyl or 1,4-phenylene whose hydrogen atoms may be substituted by fluorine atoms; ring H represents trans-cyclohexane-1,4-diyl or 1,4-phenylene; $Z^3$ represents —(CH$_2$)$_2$—, —COO—, or a single bond; $L^3$, $L^4$, and $L^5$ independently represent a hydrogen atom or a fluorine atom; b, c, and d independently represent 0 or 1; and any atom of this compound may be substituted by an isotope thereof.

5. A liquid crystal composition containing as the first component thereof at least one of the compounds according to claim 1, as a second component thereof at least one of the compounds selected from the group consisting of compounds represented by general formulas (2), (3), or (4)

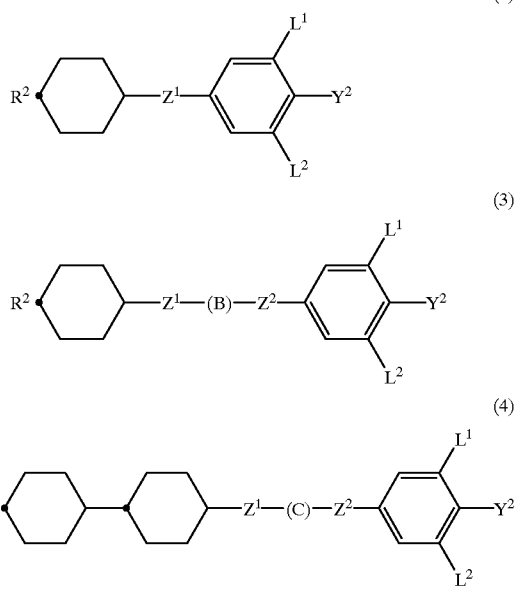

(2)

(3)

(4)

where, $R^2$ represents an alkyl group having 1 to 10 carbon atoms, in which one or more nonadjacent methylene groups in said alkyl group may be substituted by an oxygen atom or —CH=CH—, and one or more hydrogen atoms in the alkyl group may be substituted by a fluorine atom; $Y^2$ represents a fluorine atom, a chlorine atom, —OCF$_3$, —OCF$_2$H, —CF$_3$, —CF$_2$H, —CFH$_2$, —OCF$_2$ CF$_2$ H, or —OCF$_2$CFHCF$_3$; $L^1$ and $L^2$ independently represent a hydrogen atom or a fluorine atom; $Z^1$ and $Z^2$ independently represent —(CH$_2$)$_2$—, —(CH$_2$)$_4$—, —COO—, —CF$_2$O—, —OCF$_2$—, —CH=CH—, or a single bond; ring B represents trans-cyclohexane-1,4-diyl, 1,3-dioxane-2,5-diyl, or 1,4-phenylene whose hydrogen atoms may be substituted by fluorine atoms; ring C represents trans-cyclohexane-1,4-diyl, or 1,4-phenylene whose hvdroqen atoms may be substituted by fluorine atoms, and as the third component thereof at least one of the compounds selected from the group consisting of compounds represented by general formulas (7), (8) [and] or (9),

 (7)

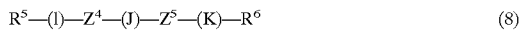 (8)

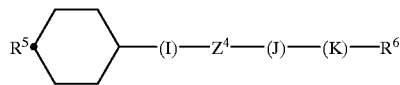

(9)

where, $R^5$ and $R^6$ independently represent an alkyl group having 1 to 10 carbon atoms, in which one or more nonadjacent methylene groups in said alkyl group may be substituted by an oxygen atom or —CH=CH—, and one or more hydrogen atoms in the alkyl group may be substituted by a fluorine atom; rings I, J, and K independently represent trans-cyclohexane-1,4-diyl, pyrimidine-2,5-diyl or 1,4-phenylene whose hydrogen atoms may be substituted by fluorine atoms; $Z^4$ and $Z^5$ independently represent —C≡C—, —COO—, —(CH$_2$)$_2$—, —CH=CH—, or a single bond; and any atom of this compound may be substituted by an isotope thereof.

6. A liquid crystal composition containing as the first component thereof at least one of the compounds according to claim 1, and as the second component thereof at least one of the compounds selected from the group consisting of compounds represented by general formulas (10), (11), or (12),

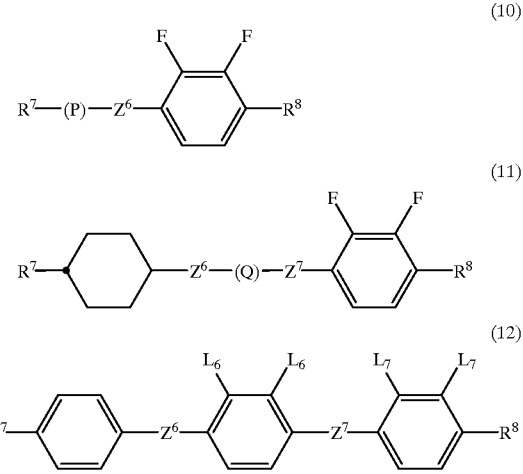

(10)

(11)

(12)

where, $R^7$ and $R^8$ independently represent an alkyl group having 1 to 10 carbon atoms, in which one or more nonadjacent methylene groups in said alkyl group may be substituted by an oxygen atom or —CH=CH—, and one or more hydrogen atoms in the alkyl group may be substituted by a fluorine atom; rings P and Q independently represent trans-cyclohexane-1,4-diyl or 1,4-phenylene; $L_6$ and $L_7$ independently represent a hydrogen atom or a fluorine atom, but do not represent hydrogen atoms at the same time; $Z^6$ and $Z^7$ independently represent —(CH$_2$)$_2$—, —COO—, or a single bond; and any atom of this compound may be substituted by an isotope thereof.

7. A liquid crystal composition containing as the first component thereof at least one of the compounds according to claim 1, as the second component thereof at least one of the compounds selected from the group consisting of compounds represented by general formulas (7), (8), or (9)

 (7)

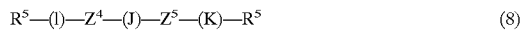 (8)

(9)

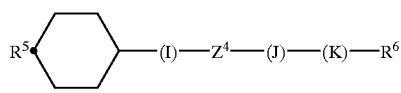

where, $R^5$ and $R^6$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group m may be substituted by a fluorine atom; rings I, J, and K independently represent trans-cyclohexane-1,4-diyl, pyrimidine-2,5-diyl or 1,4-phenylene whose hydrogen atoms may be substituted by fluorine atoms; $Z^4$ and $Z^5$ independently represent —C≡C—, —COO—, —(CH$_2$)$_2$—, —CH═CH—, or a single bond, and as the third component thereof at least one of the compounds selected from the group consisting of compounds represented by the general formulas (10), (11) or (12), (10)

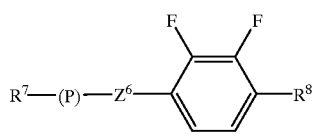

(11)

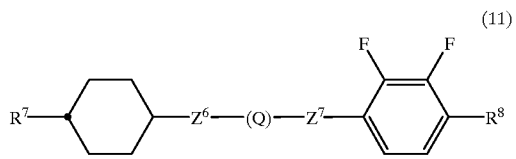

(12)

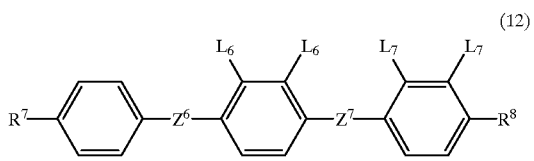

where, $R^7$ and $R^8$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group may be substituted by a fluorine atom; rings P and Q independently represent trans-cyclohexane-1,4-diyl or 1,4-phenylene; $L_6$ and $L_7$ independently represent a hydrogen atom or a fluorine atom, but do not represent hydrogen atoms at the same time; $Z^6$ and $Z^7$ independently represent —(CH$_2$)$_2$—, —COO—, or a single bond; and any atom of this compound may be substituted by an isotope thereof.

8. A liquid crystal composition containing as the first component thereof at least one of the compounds according to claim 1, as the second component thereof at least one of the compounds selected from the group consisting of compounds represented by general formulas (5) or (6)

(5)

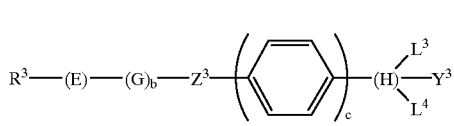

(6)

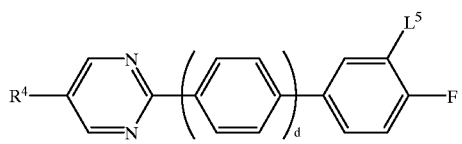

where, $R^3$ and $R^4$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group may be substituted by a fluorine atom; $Y^3$ is a cyano group or —C≡C—CN; ring E represents trans-cyclohexane-1,4-diyl, 1,4-phenylene, 1,3-dioxane-2,5-iyl, or pyrimidine-2,5-diyl; ring G represents trans-cyclohexane-1,4-diyl, pyrimidine-2,5-diyl or 1,4-phenylene whose hydrogen atoms may be substituted by fluorine atoms; ring H represents trans-cyclohexane-1,4-diyl or 1-4-phenylene; Z3 represents —(CH$_2$)$_2$—, —COO—, or a single bond; $L^3$, $L^4$, and $L^5$ independently represent a hydrogen atom or a fluorine atom; b, c, and d independently represent 0 or 1, and as the third component thereof at least one of the compounds selected from the group consisting of compounds represented by general formulas (7), (8), or (9)

 (7)

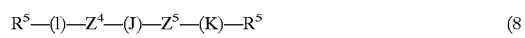 (8)

(9)

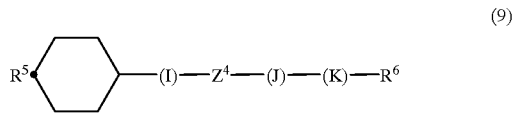

where, $R^5$ and $R^6$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group m may be substituted by a fluorine atom; rings I, J, and K independently represent trans-cyclohexane-1,4-diyl, pyrimidine-2,5-diyl or 1,4-phenylene whose hydrogen atoms may be substituted by fluorine atoms; $Z^4$ and $Z^5$ independently represent —C≡C—, —COO—, —(CH$_2$)$_2$—, —CH═CH—, or a single bond.

9. A liquid crystal composition containing as the first component thereof at least one of the compounds according to claim 1, as the second component thereof at lest one of the compounds selected from the group consisting of compounds represented by general formulas (2), (3), or (4)

(2)

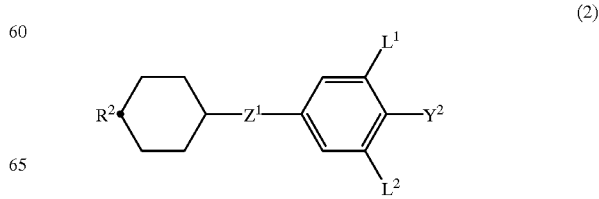

(3)

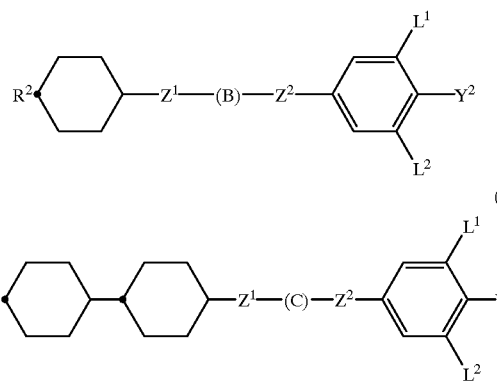

(4)

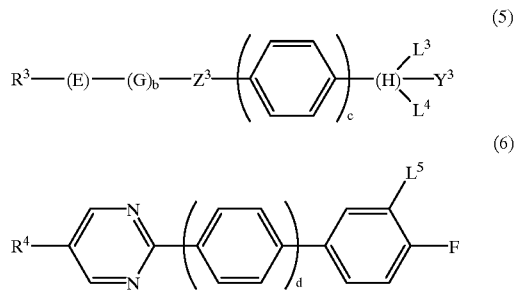

where, $R^2$ represents an alkyl group having 1 to 10 carbon atoms, in which one or more nonadjacent methylene groups in said alkyl group may be substituted by an oxygen atom or —CH═CH—, and one or more hydrogen atoms in the alkyl group may be substituted by a fluorine atom; $Y^2$ represents a fluorine atom, a chlorine atom, —OCF$_3$, —OCF$_2$H, —CF$_3$, —CF$_2$H, —CFH$_2$, —OCF$_2$CF$_2$H, or —OCF$_2$CFHCF$_3$; $L^1$ and $L^2$ independently represent a hydrogen atom or a fluorine atom; $Z^1$ and $Z^2$ independently represent —(CH$_2$)$_2$—, —(CH$_2$)$_4$—, —COO—, —CF$_2$O—, —OCF$_2$—, —CH═CH—, or a single bond; ring B represents trans-cyclohexane-1,4-diyl, 1,3-dioxane-2,5-diyl, or 1,4-phenylene whose hydrogen atoms m may be substituted by fluorine atoms; ring C represents trans-cyclohexane-1,4-diyl, or 1,4-phenylene whose hydrogen atoms may be substituted by fluorine atoms, as the third component thereof at least one of the compounds selected from the group consisting of compounds represented by general formulas (5) or (6)

 (5)

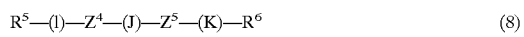 (6)

where, $R^3$ and $R^4$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group may be substituted by a fluorine atom; $Y^3$ is a cyano group or —C≡C—CN; ring E represents trans-cyclohexane-1,4-diyl, 1,4-phenylene, 1,3-dioxane-2,5-iyl, or pyrimidine-2,5-diyl; ring G represents trans-cyclohexane-1,4-diyl, pyrimidine-2,5-diyl or 1,4-phenylene whose hydrogen atoms may be substituted by fluorine atoms; ring H represents trans-cyclohexane-1,4-diyl or 1-4-phenylene; $Z^3$ represents —(CH$_2$)$_2$—, —COO—, or a single bond; $L^3$, $L^4$, and $L^5$ independently represent a hydrogen atom or a fluorine atom; b, c, and d independently represent 0 or 1, and as the fourth component thereof at least one of the compounds selected from the group consisting of compounds represented by general formulas (7), (8) or (9), $$R^5-(I)-Z^4-(J)-Z^5-R^6 \quad (7)$$

$$R^5-(I)-Z^4-(J)-Z^5-(K)-R^6 \quad (8)$$

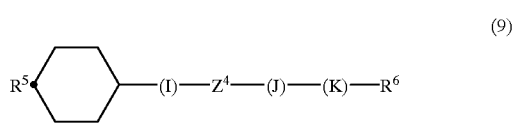 (9)

where, $R^5$ and $R^6$ independently represent an alkyl group having 1 to 10 carbon atoms, in which one or more nonadjacent methylene groups in said alkyl group may be substituted by an oxygen atom or —CH═CH—, and one or more hydrogen atoms in the alkyl group m may be substituted by a fluorine atom; rings I, J, and K independently represent trans-cyclohexane-1,4-diyl, pyrimidine-2,5-diyl or 1,4-phenylene whose hydrogen atoms may be substituted by fluorine atoms; $Z^4$ and $Z^5$ independently represent —C≡C—, —COO—, —(CH$_2$)$_2$—, —CH═CH—, or a single bond; and any atom of this compound may be substituted by an isotope thereof.

10. A liquid crystal composition containing at least one optically active compound in addition to a liquid crystal composition according to claim 2.

11. A liquid crystal display element fabricated utilizing a liquid crystal composition according to claim 2.

12. A liquid crystal composition containing at least one optically active compound in addition to a liquid crystal composition according to claim 3.

13. A liquid crystal display element fabricated utilizing a liquid crystal composition according to claim 3.

14. A liquid crystal composition containing at least one optically active compound in addition to a liquid crystal composition according to claim 4.

15. A liquid crystal display element fabricated utilizing a liquid crystal composition according to claim 4.

16. A liquid crystal composition containing at least one optically active compound in addition to a liquid crystal composition according to claim 5.

17. A liquid crystal display element fabricated utilizing a liquid crystal composition according to claim 5.

18. A liquid crystal composition containing at least one optically active compound in addition to a liquid crystal composition according to claim 6.

19. A liquid crystal display element fabricated utilizing a liquid crystal composition according to claim 6.

20. A liquid crystal composition containing at least one optically active compound in addition to a liquid crystal composition according to claim 7.

* * * * *